(12) United States Patent
Marrano et al.

(10) Patent No.: US 12,350,130 B2
(45) Date of Patent: *Jul. 8, 2025

(54) HEADBOX FOR MANUFACTURING A SUBSTRATE

(71) Applicant: KIMBERLY-CLARK WORLDWIDE, INC., Neenah, WI (US)

(72) Inventors: Stephen A. Marrano, Oshkosh, WI (US); Kyle Krautkramer, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/610,725

(22) Filed: Mar. 20, 2024

(65) Prior Publication Data

US 2024/0225911 A1 Jul. 11, 2024

Related U.S. Application Data

(63) Continuation of application No. 17/928,297, filed as application No. PCT/US2021/034722 on May 28, 2021, now Pat. No. 11,963,851.

(Continued)

(51) Int. Cl.
*A61F 13/15* (2006.01)
*D21F 1/02* (2006.01)

(52) U.S. Cl.
CPC .............. *A61F 13/15* (2013.01); *D21F 1/02* (2013.01); *A61F 13/15642* (2013.01); *A61F 13/15699* (2013.01)

(58) Field of Classification Search
CPC . D21F 1/02; D21F 1/022; D21F 1/024; D21F 1/026; D21F 1/028; A61F 13/15;
(Continued)

(56) References Cited

U.S. PATENT DOCUMENTS

| 3,123,520 A | 3/1964 | Fish, Jr. |
| 3,549,742 A | 12/1970 | Benz |

(Continued)

FOREIGN PATENT DOCUMENTS

| CN | 101861427 A | 10/2010 |
| CN | 102822416 A | 12/2012 |

(Continued)

OTHER PUBLICATIONS

NCSU, "Foam (Entrained air, Visible foam)", Sep. 9, 2019, https://projects.ncsu.edu/project/hubbepaperchem/TShoot/G_Foam.htm.

(Continued)

*Primary Examiner* — Jose A Fortuna
(74) *Attorney, Agent, or Firm* — KIMBERLY-CLARK WORLDWIDE, INC.

(57) ABSTRACT

Methods and apparatuses for producing a substrate are described. A method and apparatus for introducing a component into a fluid supply is also presented. A method can include providing a first fluid supply. The fluid supply can be configured as a foam in some embodiments. The method can also include providing a component feed system and a supply of the component. The method can include introducing the component to a fluid supply in an eductor in some aspects. A resultant slurry including a fluid supply and the component can be transferred through a headbox. The resultant slurry can be dewatered to provide a substrate including the component.

20 Claims, 11 Drawing Sheets

Related U.S. Application Data

(60) Provisional application No. 63/031,803, filed on May 29, 2020.

(58) Field of Classification Search
CPC .......... A61F 13/15642; A61F 13/15699; A61F 13/53; D04H 1/425; D04H 1/732
See application file for complete search history.

(56) References Cited

U.S. PATENT DOCUMENTS

| | | | |
|---|---|---|---|
| 3,937,273 A | | 2/1976 | Radvan et al. |
| 4,021,296 A | * | 5/1977 | Reiner .................... D21F 1/028 |
| | | | 162/347 |
| 4,083,750 A | | 4/1978 | Newns et al. |
| 4,234,379 A | | 11/1980 | Conway et al. |
| 4,604,164 A | | 8/1986 | Fujiwara et al. |
| 4,765,858 A | | 8/1988 | Vankerckhoven et al. |
| 4,812,208 A | | 3/1989 | Yuasa et al. |
| 5,183,537 A | | 2/1993 | Hergert et al. |
| 5,506,035 A | | 4/1996 | Van Phan et al. |
| 5,603,807 A | * | 2/1997 | Heinzmann ............... D21F 1/02 |
| | | | 162/336 |
| 5,904,809 A | | 5/1999 | Rokman et al. |
| 6,019,871 A | | 2/2000 | Rokman et al. |
| 6,066,235 A | | 5/2000 | Scheinberg |
| 6,139,684 A | | 10/2000 | Lawson et al. |
| 6,264,796 B1 | | 7/2001 | Simmons |
| 6,372,092 B1 | | 4/2002 | Bubik et al. |
| 6,425,984 B2 | | 7/2002 | Aidun |
| 6,503,372 B1 | | 1/2003 | Rokman et al. |
| 6,518,479 B1 | | 2/2003 | Graef et al. |
| 6,603,054 B2 | | 8/2003 | Chen et al. |
| 6,679,974 B1 | * | 1/2004 | Soini ........................ D21F 1/02 |
| | | | 162/212 |
| 6,746,571 B1 | | 6/2004 | Scheinberg |
| 6,769,199 B2 | | 8/2004 | Vrbanac et al. |
| 6,962,647 B2 | * | 11/2005 | Ronnila .................. D21F 1/026 |
| | | | 162/344 |
| 7,416,636 B2 | | 8/2008 | Blomqvist et al. |
| 7,794,570 B2 | | 9/2010 | Ewald |
| 8,075,737 B2 | * | 12/2011 | Ewald ..................... D21F 1/028 |
| | | | 162/336 |
| 10,385,508 B2 | | 8/2019 | Polat et al. |
| 11,963,851 B2 | * | 4/2024 | Marrano .................. A61F 13/53 |
| 2003/0159791 A1 | | 8/2003 | Ronnila et al. |
| 2006/0148917 A1 | | 7/2006 | Radwanski et al. |
| 2012/0186767 A1 | | 7/2012 | Loser et al. |
| 2018/0140529 A1 | | 5/2018 | Miller, IV et al. |
| 2023/0201044 A1 | | 6/2023 | Marrano et al. |
| 2023/0212796 A1 | * | 7/2023 | Marrano ................. B01F 23/582 |
| | | | 162/228 |
| 2023/0212800 A1 | * | 7/2023 | Marrano ................... D04H 1/58 |
| | | | 425/200 |
| 2023/0241561 A1 | * | 8/2023 | Marrano ............... B01J 20/3208 |
| | | | 366/163.2 |
| 2024/0225911 A1 | * | 7/2024 | Marrano .................. A61F 13/53 |
| 2024/0279856 A1 | * | 8/2024 | Marrano ........... B01F 25/31243 |

FOREIGN PATENT DOCUMENTS

| | | | | |
|---|---|---|---|---|
| CN | 103382672 A | | 11/2013 | |
| CN | 203795229 U | | 8/2014 | |
| DE | 4239644 A1 | * | 6/1994 | ............... D21F 1/02 |
| DE | 19942047 A1 | | 2/2001 | |
| DE | 102008042032 A1 | | 3/2010 | |
| DE | 102011003849 A1 | | 8/2012 | |
| DE | 102018120162 A1 | | 10/2019 | |
| EP | 2589702 B1 | | 5/2016 | |
| GB | 1423874 A | | 2/1976 | |
| JP | 1994207394 A | | 7/1994 | |
| RU | 2789680 C1 | | 2/2023 | |
| WO | 2018019545 A1 | | 2/2018 | |
| WO | 2020043370 A1 | | 3/2020 | |

OTHER PUBLICATIONS

Wang, X, "On the Research Areas of Approach Flow Systems", Mar. 1996, Institute of Paper Science and Technology; Atlanta, Georgia, https://smartech.gatech.edu/bitstream/handle/1853/774/F004-1—1996-03.pdf.

* cited by examiner

HEADBOX FOR MANUFACTURING A SUBSTRATE

TECHNICAL FIELD

The present disclosure relates to methods and apparatuses for forming substrates. More specifically, the present disclosure relates to foam-forming methods and apparatuses for forming substrates.

BACKGROUND OF THE DISCLOSURE

Personal care products, such as diapers, diaper pants, training pants, adult incontinence products, and feminine care products, can include a variety of substrates. For example, a diaper can include an absorbent structure, nonwoven materials, and films. Similarly, facial tissues, wipes, and wipers can also include various substrates. Some of the substrates in these products can include natural and/or synthetic fibers. In some products, some substrates can also include different types of components to provide additional functionality to the substrate and/or the end product itself.

For example, one such component that may be desirable to add to a substrate includes a superabsorbent material (SAM). SAM can be configured in the form of a particle or a fiber and is commonly utilized in substrates for increased absorbent capacity. Absorbent systems of personal care absorbent products, such as a diaper, often include SAM. Processes exist for forming a substrate with SAM, including utilizing forming chambers to mix SAM particles or fibers with cellulosic fibers to form an absorbent core. These processes are generally completed in a dry environment, as SAM can be difficult to process when wet due to increase in volume from absorption of fluid and gelling, among other potential drawbacks. However, alternative substrate forming processes can employ fluids, such as liquids, to create substrates providing various other characteristics and efficiencies in manufacturing and performance of such substrates.

Thus, there exists a need to develop methods and apparatuses for introducing a component into a fluid supply for forming substrates. There also exists a need to develop methods and apparatuses for forming substrates including components. There also exists a need to develop improved headboxes for forming substrates.

SUMMARY OF THE DISCLOSURE

In one embodiment, a headbox is provided. The headbox can include a machine direction and a cross direction. The headbox can further include at least one flow section. The at least one flow section can include a bottom surface and a top surface. The top surface can be opposite from the bottom surface. The at least one flow section can include a first side and a second side. The second side can be opposite from the first side and spaced apart from the first side in the cross direction. The first side and the second side can each comprise a first portion being convex to an interior of the at least one flow section and a second portion being concave to the interior of the at least one flow section.

In another embodiment, a headbox is provided. The headbox can include a machine direction and a cross direction. The headbox can also include a first flow section and a second flow section. The first flow section and second flow section can each include a bottom surface and a top surface. The top surface can be opposite from the bottom surface. The first flow section and second flow section can each include a first side and a second side. The second side can be opposite from the first side and spaced apart from the first side in the cross direction. The first side and the second side each include a first portion being convex to an interior of the at least one flow section and a second portion being concave to the interior of the at least one flow section.

In still another embodiment, a headbox is provided. The headbox can include a machine direction and a cross direction. The headbox can include at least one flow section. The at least one flow section can include an interior. The interior can include a machine directional side profile including a first side profile and a second side profile. The second side profile can be opposite from the first side profile and spaced apart from the first side profile in the cross direction. The first side profile and the second side profile can each include a first portion being convex to the interior of the at least one flow section and a second portion being concave to the interior of the at least one flow section.

BRIEF DESCRIPTION OF THE DRAWINGS

A full and enabling disclosure thereof, directed to one of ordinary skill in the art, is set forth more particularly in the remainder of the specification, which makes reference to the appended figures in which.

Figure 1:
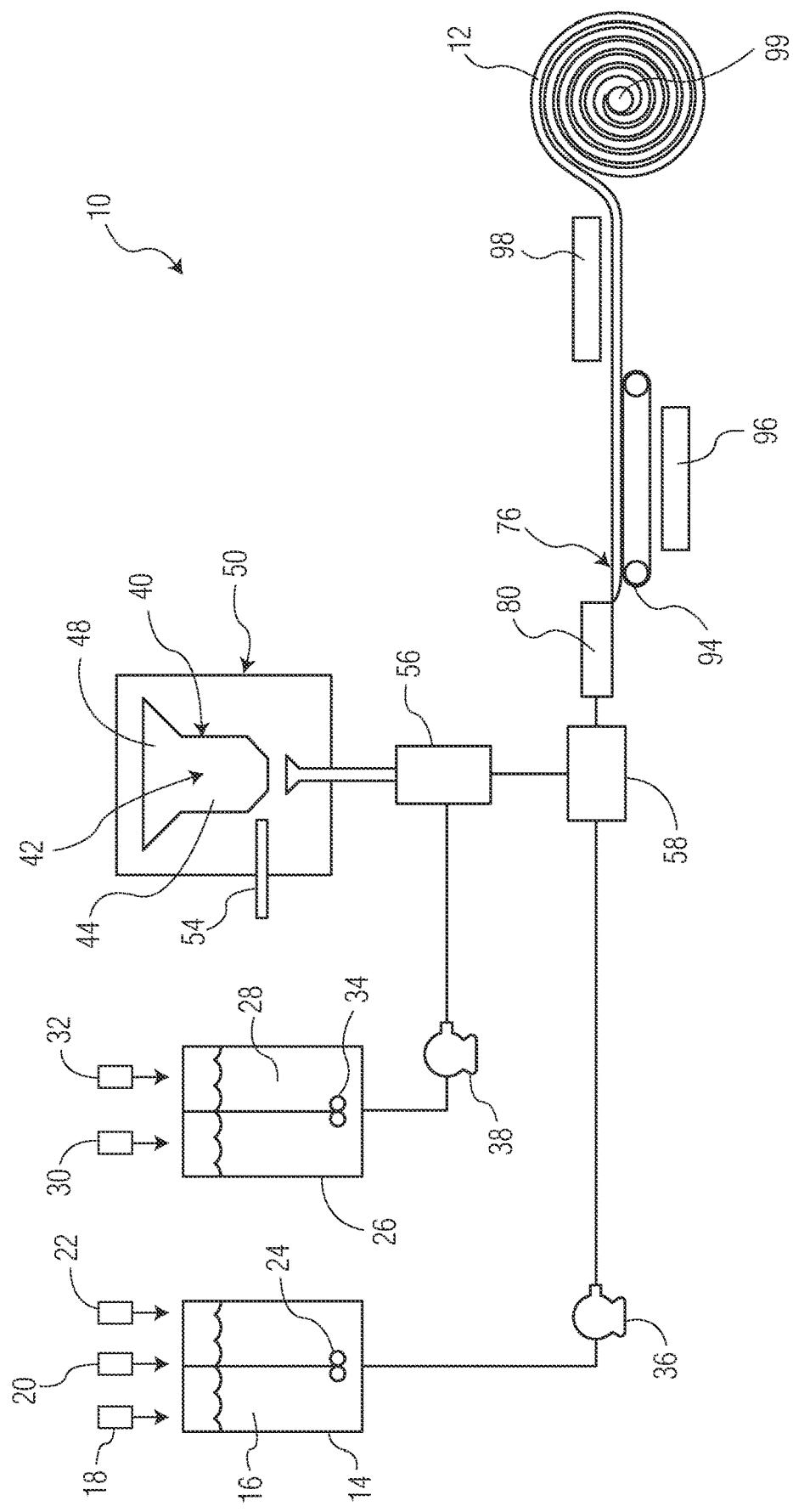
FIG. 1 is a process schematic of an exemplary method for introducing a component into a fluid supply and forming a substrate including a component according to one embodiment of the present disclosure.

Repeat use of reference characters in the present specification and drawings is intended to represent the same or analogous features or elements of the disclosure.

DETAILED DESCRIPTION OF THE DISCLOSURE

The present disclosure is directed to methods and apparatuses that can produce a substrate including a component. While the present disclosure provides examples of substrates manufactured through foam-forming, it is contemplated that the methods and apparatuses described herein may be utilized to benefit wet-laid and/or air-laid manufacturing processes.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. As used herein, the terminology of "first," "second," "third", etc. does not designate a specified order, but is used as a means to differentiate between different occurrences when referring to various features in the present disclosure. Many modifications and variations of the present disclosure can be made without departing from the spirit and scope thereof. Therefore, the exemplary embodiments described herein should not be used to limit the scope of the invention.

Definitions

As used herein, the term "foam formed product" means a product formed from a suspension including a mixture of a solid, a liquid, and dispersed gas bubbles.

As used herein, the term "foam forming process" means a process for manufacturing a product involving a suspension including a mixture of a solid, a liquid, and dispersed gas bubbles.

As used herein, the term "foaming fluid" means any one or more known fluids compatible with the other components in the foam forming process. Suitable foaming fluids include, but are not limited to, water.

As used herein, the term "foam half life" means the time elapsed until the half of the initial frothed foam mass reverts to liquid water.

As used herein, the term "layer" refers to a structure that provides an area of a substrate in a z-direction of the substrate that is comprised of similar components and structure.

As used herein, the term "nonwoven web" means a web having a structure of individual fibers or threads which are interlaid, but not in an identifiable manner as in a knitted web.

As used herein, unless expressly indicated otherwise, when used in relation to material compositions the terms "percent", "%", "weight percent", or "percent by weight" each refer to the quantity by weight of a component as a percentage of the total except as whether expressly noted otherwise.

The term "personal care absorbent article" refers herein to an article intended and/or adapted to be placed against or in proximity to the body (i.e., contiguous with the body) of the wearer to absorb and contain various liquid, solid, and semi-solid exudates discharged from the body. Examples include, but are not limited to, diapers, diaper pants, training pants, youth pants, swim pants, feminine hygiene products, including, but not limited to, menstrual pads or pants, incontinence products, medical garments, surgical pads and bandages, and so forth.

The term "ply" refers to a discrete layer within a multi-layered product wherein individual plies may be arranged in juxtaposition to each other.

The term "plied" or "bonded" or "coupled" refers herein to the joining, adhering, connecting, attaching, or the like, of two elements. Two elements will be considered plied, bonded or coupled together when they are joined, adhered, connected, attached, or the like, directly to one another or indirectly to one another, such as when each is directly bonded to intermediate elements. The plying, bonding or coupling of one element to another can occur via continuous or intermittent bonds.

The term "superabsorbent material" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

Method and Apparatus

In one embodiment, the present disclosure relates to a method and apparatus 10 that can form a substrate 12. FIG. 1 provides a schematic of an exemplary apparatus 10 that can be used as part of a foam forming process to manufacture a substrate 12 that is a foam formed product. The apparatus 10 can include a first tank 14 configured for holding a first fluid supply 16. In some embodiments, the first fluid supply 16 can be a foam. The first fluid supply 16 can include a fluid provided by a supply of fluid 18. In some embodiments, the first fluid supply 16 can include a plurality fibers provided by a supply of fibers 20, however, in other embodiments, the first fluid supply 16 can be free from a plurality of fibers. The first fluid supply 16 can also include a surfactant provided by a supply of surfactant 22. In some embodiments, the first tank 14 can include a mixer 24, as will be discussed in more detail below. The mixer 24 can mix (e.g., agitate) the first fluid supply 16 to mix the fluid, fibers (if present), and surfactant with air, or some other gas, to create a foam. The mixer 24 can also mix the foam with fibers (if present) to create a foam suspension of fibers in which the foam holds and separates the fibers to facilitate a distribution of the fibers within the foam (e.g., as an artifact of the mixing process in the first tank 14). Uniform fiber distribution can promote desirable substrate 12 including, for example, strength and the visual appearance of quality.

The apparatus 10 can also include a second tank 26 configured for holding a second fluid supply 28. In some embodiments, the second fluid supply 28 can be a foam. The second fluid supply 28 can include a fluid provided by a supply of fluid 30 and a surfactant provided by a supply of surfactant 32. In some embodiments, the second fluid supply 28 can include a plurality of fibers in addition to or as an alternative to the fibers being present in the first fluid supply 16. In some embodiments, the second tank 26 can include a mixer 34. The mixer 34 can mix the second fluid supply 28 to mix the fluid and surfactant with air, or some other gas, to create a foam.

For either or both the first tank 14 and the second tank 26, the first fluid supply 16 or the second fluid supply 28 can be acted upon to form a foam. In some embodiments, the foaming fluid and other components are acted upon so as to form a porous foam having an air content greater than about 50% by volume and desirably an air content greater than about 60% by volume. In certain aspects, the highly-expanded foam is formed having an air content of between about 60% and about 95% and in further aspects between about 65% and about 85%. In certain embodiments, the foam may be acted upon to introduce air bubbles such that the ratio of expansion (volume of air to other components in the expanded stable foam) is greater than 1:1 and in certain embodiments the ratio of air:other components can be between about 1.1:1 and about 20:1 or between about 1.2:1 and about 15:1 or between about 1.5:1 and about 10:1 or even between about 2:1 and about 5:1.

The foam can be generated by one or more means known in the art. Examples of suitable methods include, without limitation, aggressive mechanical agitation such as by mixers 24, 34, injection of compressed air, and so forth. Mixing the components through the use of a high-shear, high-speed mixer is particularly well suited for use in the formation of the desired highly-porous foams. Various high-shear mixers are known in the art and believed suitable for use with the present disclosure. High-shear mixers typically employ a tank holding the foam precursor and/or one or more pipes through which the foam precursor is directed. The high-shear mixers may use a series of screens and/or rotors to work the precursor and cause aggressive mixing of the components and air. In a particular embodiment, the first tank 14 and/or the second tank 26 is provided having therein one or more rotors or impellors and associated stators. The rotors or impellors are rotated at high speeds in order to cause flow and shear. Air may, for example, be introduced into the tank at various positions or simply drawn in by the action of the mixers 24, 34. While the specific mixer design may influence the speeds necessary to achieve the desired mixing and shear, in certain embodiments suitable rotor speeds may be greater than about 500 rpm and, for example, be between about 1000 rpm and about 6000 rpm or between about 2000 rpm and about 4000 rpm. In certain embodiments, with respect to rotor based high-shear mixers, the mixer(s) 24, 34 may be run with the foam until the disappearance of the vortex in the foam or a sufficient volume increase is achieved.

In addition, it is noted the foaming process can be accomplished in a single foam generation step or in sequential foam generation steps for the first tank 14 and/or the second tank 26. For example, in one embodiment, all of the components of the first fluid supply 16 in the first tank 14 (e.g., the supply of the fluid 18, fibers 20, and surfactant 22) may be mixed together to form a slurry from which a foam is formed. Alternatively, one or more of the individual components may be added to the foaming fluid, an initial mixture formed (e.g. a dispersion or foam), after which the remaining components may be added to the initially foamed slurry and then all of the components acted upon to form the final foam. In this regard, the fluid 18 and surfactant 22 may be initially mixed and acted upon to form an initial foam prior to the addition of any solids. Fibers, if desired, may then be added to the water/surfactant foam and then further acted upon to form the final foam. As a further alternative, the fluid 18 and fibers 20, such as a high density cellulose pulp sheet, may be aggressively mixed at a higher consistency to form an initial dispersion after which the foaming surfactant, additional water and other components, such as synthetic fibers, are added to form a second mixture which is then mixed and acted upon to form the foam.

The foam density of the foam forming the first fluid supply 16 in the first tank 14 and/or the foam forming the second fluid supply 28 in the second tank 26 can vary depending upon the particular application and various factors, such as the fiber stock used. In some implementations, for example, the foam density of the foam can be greater than about 100 g/L, such as greater than about 250 g/L, such as greater than about 300 g/L. The foam density is generally less than about 800 g/L, such as less than about 500 g/L, such as less than about 400 g/L, such as less than about 350 g/L. In some implementations, for example, a lower density foam is used having a foam density of generally less than about 350 g/L, such as less than about 340 g/L, such as less than about 330 g/L.

In some embodiments, the apparatus 10 can also include a first pump 36 and a second pump 38. The first pump 36 can be in fluid communication with the first fluid supply 16 and can be configured for pumping the first fluid supply 16 to transfer the first fluid supply 16. The second pump 38 can be in fluid communication with the second fluid supply 28 and can be configured for pumping the second fluid supply 28 to transfer the second fluid supply 28. In some embodiments, the first pump 36 and/or the second pump 38 can be a progressive cavity pump or a centrifugal pump, however, it is contemplated that other suitable types of pumps can be used. Additionally, as discussed further below, in some embodiments, the apparatus can be provided with a single pump that can pump a single fluid supply into a first fluid supply 16 and a second fluid supply 28.

Figure 2:
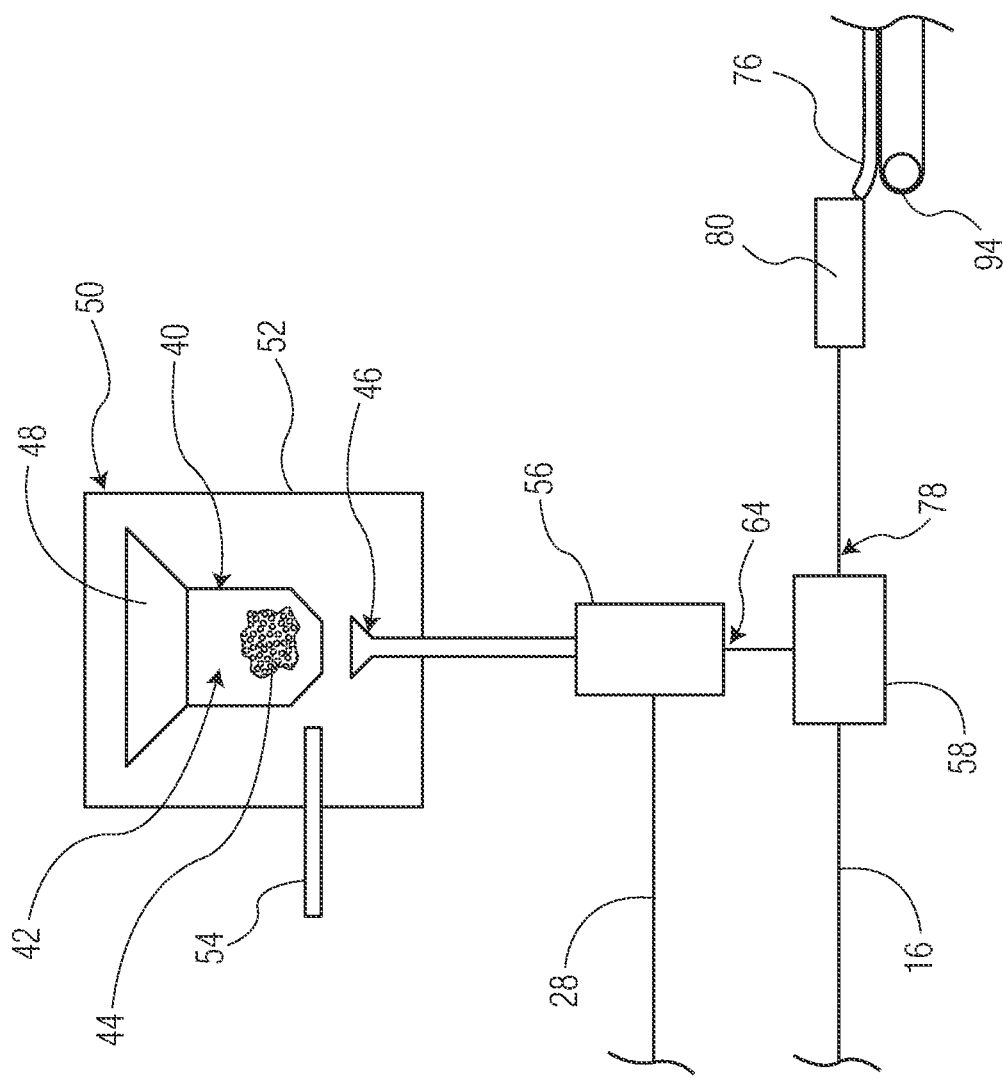
FIG. 2 is a detailed schematic of the component feed system, two mixing junctions, and two fluid supplies upstream of the headbox as depicted from the process schematic in FIG. 1.

As depicted in FIGS. 1 and 2, the apparatus 10 can also include a component feed system 40. The component feed system 40 can include a component supply area 42 for receiving a supply of a component 44 as shown in the partial cut-away portion of the component supply area 42 illustrated in FIG. 2. The component feed system 40 can also include an outlet conduit 46. The outlet conduit 46 can be circular in cross-sectional shape, or can be configured in a rectangular fashion such as to form a slot. The component feed system 40 can also include a hopper 48. The hopper 48 can be coupled to the component supply area 42 and can be utilized for refiling the supply of the component 44 to the component supply area 42.

In some embodiments, the component feed system 40 can include a bulk solids pump. Some examples of bulk solids pumps that may be used herein can include systems that utilize screws/augers, belts, vibratory trays, rotating discs, or other known systems for handling and discharging the supply of the component 44. Other types of feeders can be used for the component feed system 40, such as, for example, an ingredient feeder, such as those manufactured by Christy Machine & Conveyor, Fremont, Ohio. The component feed system 40 can also be configured as a conveyor system in some embodiments.

The component feed system 40 can also include a fluid control system 50. The fluid control system 50 can be configured to control the gas entrainment into the fluid supply into which the supply of the component 44 is being placed. In some embodiments, the fluid control system 50 can include a housing 52. The housing 52 can form a pressurized seal volume around the component feed system 40. In other embodiments, the fluid control system 50 can be formed as an integral part to the structure component feed system 40 itself, such that a separate housing 52 surrounding the component feed system 40 may not be required. As depicted in FIGS. 1 and 2, the fluid control system 50 can also include a bleed orifice 54 in some embodiments.

The supply of the component 44 can be in the form of a particulate and/or a fiber. In one embodiment as described herein, the supply of the component 44 can be superabsorbent material (SAM) in particulate form. In some embodiments, SAM can be in the form of a fiber. Of course, other types of components, as described further below, are also contemplated as being utilized in the apparatus 10 and methods as described herein. The component feed system 40 as described herein can be particularly beneficial for a supply of component 44 that is most suitably maintained in a dry environment with minimal of exposure to fluid or foam utilized in the apparatus 10 and methods described herein.

Figure 3:
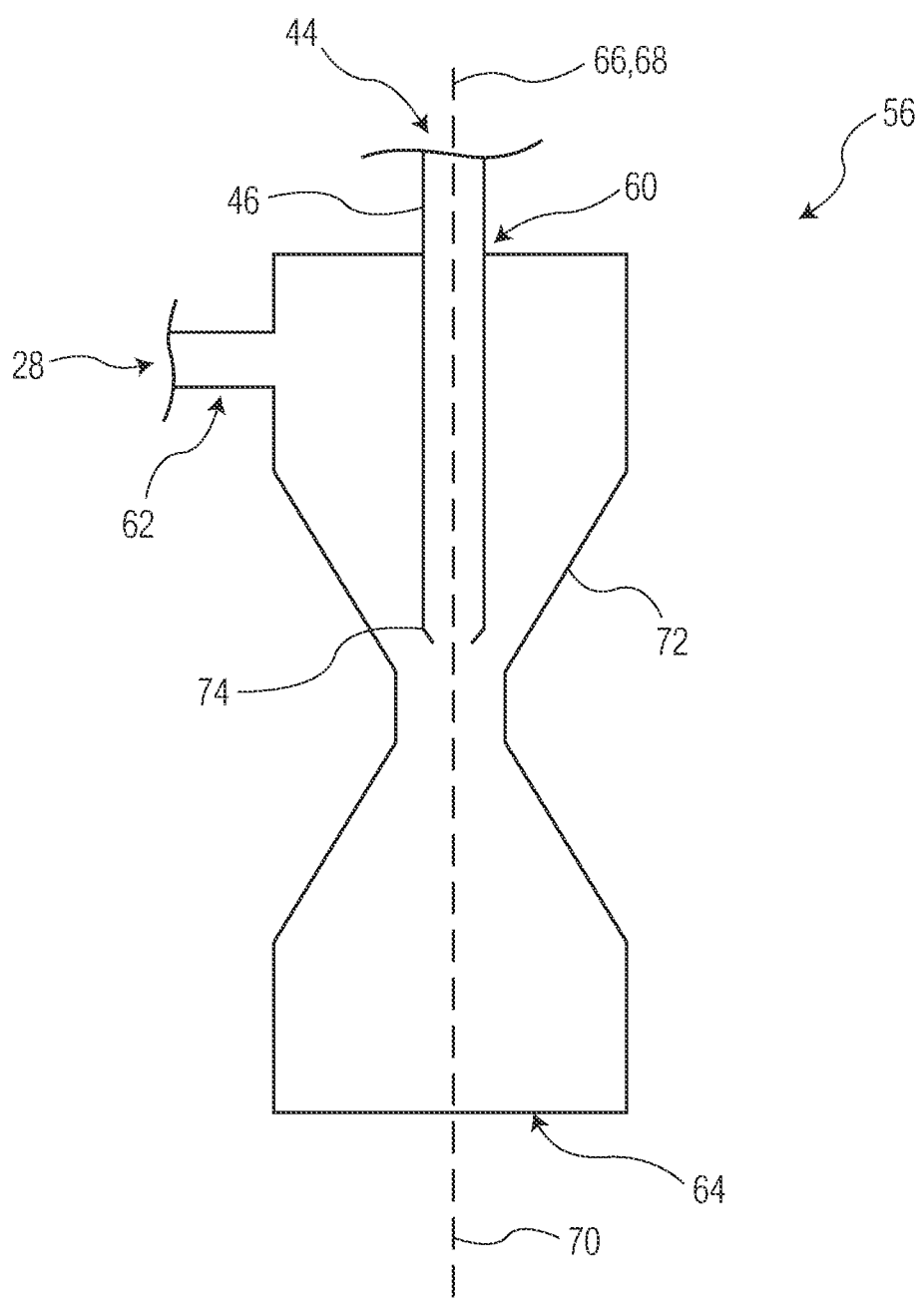
FIG. 3 is a cross-section of the first mixing junction and outlet conduit of the component feed system of FIG. 2.

Referring to FIGS. 1-3, in some embodiments, the apparatus 10 and methods described herein can include a first mixing junction 56 and a second mixing junction 58. In preferred embodiments, the first mixing junction 56 can be an eductor. The first mixing junction 56 can be in fluid communication with the outlet conduit 46 of the component feed system 40 and in fluid communication with the second fluid supply 28. As depicted in FIG. 3, the first mixing junction 56 can include a first inlet 60 and a second inlet 62. The first inlet 60 can be in fluid communication with the supply of the component 44 via the outlet conduit 46. The second inlet 62 can be in fluid communication with the second fluid supply 28. The first mixing junction 56 can also include a discharge 64.

In preferred embodiments, the first mixing junction 56 can be configured as a co-axial eductor. For example, in a preferred embodiment, the first mixing junction 56 can be configured such that the first inlet axis 66 of the first inlet 60 of the first mixing junction 56 is co-axial with the outlet axis 68 of outlet conduit 46 that provides the supply of the component 44. The first mixing junction 56 can also be configured such that the discharge axis 70 of the discharge 64 is co-axial with the outlet axis 68 of the outlet conduit 46. As such, the first mixing junction 56 can be configured such that the first inlet axis 66 of the first inlet 60 can be co-axial with the discharge axis 70 of the discharge 64 of the first mixing junction 56. The second inlet 62 providing the second fluid supply 28 to the first mixing junction 56 can be set up to enter the first mixing junction 56 on a side of the first mixing junction 56. This configuration of having the supply of the component 44 be delivered in the first inlet 60 in a co-axial fashion to the discharge axis 70, rather than having the second fluid supply 28 entering at the first inlet 60, is opposite of most eductor configurations that are mixing a fluid supply and a component using a motive force of the fluid supply, but provides advantages to the first mixing junction 56 as described herein.

When configured as an eductor, the first mixing junction 56 can mix the supply of the component 44 from the component feed system 40 with the second fluid supply 28. By transferring the second fluid supply 28 into the first mixing junction 56 at the second inlet 62 and through the first mixing junction 56, the second fluid supply 28 provides a motive pressure to the supply of the component 44. The motive pressure can create a vacuum on the supply of the component 44 and the component feed system 40 to help draw the supply of the component 44 to mix and be entrained in the second fluid supply 28. In some embodiments, the motive pressure can create a vacuum on the supply of the component 44 of less than 1.5 in Hg, however, in other embodiments, the motive pressure could create a vacuum on the supply of the component 44 of 5 in. Hg or more, or 10 in Hg or more.

The fluid control system 50 can help manage proper distribution and entrainment of the supply of the component 44 to the second fluid supply 28 and can help control entrainment of fluid within the second fluid supply 28 downstream of the component feed system 40. For example, if there was no housing 52 surrounding the component feed system 40, additional fluid (e.g., surrounding gas, such as air) may be entrained into the second fluid supply 28 as the supply of the component 44 is metered into the second fluid supply 28. It may also be the case when the second fluid supply 28 creates a motive pressure on the component feed system 40, the vacuum pulling on the supply of the component 44 may cause additional air to be entrained in the second fluid supply 28. In some circumstances, entraining additional air in the second fluid supply 28 may be desired, however, in other circumstances, it may be desirable to control the gas content of the second fluid supply 28 while inputting the supply of the component 44 to the second fluid supply 28 at the first mixing junction 56. For example, in some circumstances where the second fluid supply 28 is a foam, the amount of gas content in the foam may be desired to be kept relatively fixed as the foam passes through the first mixing junction 56. Thus, the fluid control system 50 can help control the pressure on and the gas flow through the component feed system 40 to help prevent or at least control the amount of gas being entrained in the second fluid supply 28 when the supply of the component 44 is being mixed with the second fluid supply 28, and can help counteract the motive pressure on the supply of the component 44 and the component feed system 40 created by the second fluid supply 28.

In some embodiments, the fluid control system 50 can include sealing off the component feed system 40. For example, as discussed above, the fluid control system 50 can include a housing 52 to provide a seal on the component feed system 40. Sealing the component feed system 40 can help to prevent additional air entrainment in the second fluid supply 28 when the supply of the component 44 is introduced into the second fluid supply 28 in the first mixing junction 56.

However, in some embodiments, it may be beneficial to also include additional capability to the fluid control system 50. For example, in some embodiments, the fluid control system 50 can include a bleed orifice 54. The bleed orifice 54 can be configured to bleed-in fluid flow, such as atmospheric air flow, to provide additional fluid flow control of the component feed system 40. The bleed orifice 54 can bleed in gas flow (e.g., air flow) inside the housing 52 to help control the air flow and pressure within the housing 52 surrounding the component feed system 40. It has been discovered that by providing a bleed-in orifice 54 to provide some bleed-in of atmospheric air flow to the component feed system 40, back-splashing of the second fluid supply 28 in the first mixing junction 56 can be reduced or eliminated. Reducing back-splashing of the second fluid supply 28 in the first mixing junction 56 can help prevent the component feed system 40 from becoming clogged or needing to be cleaned, especially where the component feed system 40 may be delivering a dry particulate, such as SAM. Under other process conditions, it may be desirable to completely seal the component feed system 40 for similar reasons.

Additionally or alternatively, the fluid control system 50 can be configured to provide additional gas flow (e.g., air flow) and/or positive pressure to prevent back-filling of the component feed system 40 in some circumstances, such as if a downstream obstruction occurs in the apparatus 10 beyond the first mixing junction 56. In such a case of an obstruction creating an increased pressure, the second fluid supply 28 may have a desire to back-fill the component feed system 40. Back-filling of fluid into the component feed system 40 can be detrimental to processing, especially where the supply of the component 44 is a dry component, such as SAM. A fluid control system 50 configured to be able to provide positive pressure to the component feed system 40 can help prevent such back-filling of the component feed system 40.

It is also contemplated that other additional aspects of a fluid control system 50 could be utilized to maintain the gas flow and pressure to a suitable level for the component feed system 40, including, but not limited to, supplying vacuum to the component feed system 40 in addition to or alternative to the air bleed-in at the bleed orifice 54 and/or the positive pressure described above.

As depicted in FIG. 3, in some embodiments, the first mixing junction 56 can also include a venturi section 72. The venturi section 72 can be a necked region of the first mixing junction 56 that can increase the velocity of the second fluid supply 28 passing through the venturi section 72, and thus, can increase the vacuum pressure created by the second fluid supply 28 on the supply of the component 44 in the component feed system 40 and can help entrain the supply of the component 44 within the second fluid supply 28. In some embodiments, the distal end 74 of the outlet conduit 46 providing the supply of the component 44 to the first mixing junction 56 can be disposed in the venturi section 72. The location of the distal end 74 of the outlet conduit 46 can be adjusted within the venturi section 72 as one way to control both the pressure of the second fluid supply 28 as it is discharged from the first mixing junction 56 and the component feed system 40.

The first mixing junction 56 can also provide pressure control on the transfer of the second fluid supply 28 including the component 44 as it exits the discharge 64 of the first mixing junction 56 as compared to when the second fluid supply 28 enters the first mixing junction 56. The second fluid supply 28 can be transferred at a second fluid pressure prior to the first mixing junction 56. The second fluid supply 28 including the component from the supply of the component 44 can exit the discharge 64 of the first mixing junction 56 at a discharge pressure. The pressure difference between the second fluid pressure prior to the first mixing junction 56 and the discharge pressure can be controlled. In some embodiments, this pressure difference can be controlled by varying the flow rate of the second fluid supply 28. In some embodiments, this pressure difference can be controlled by the location of the distal end 74 of the outlet conduit 46 in the venturi section 72 of the first mixing junction 56. For example, if the distal end 74 of the outlet conduit 46 is moved further into the venturi section 72, the area for the second fluid supply 28 to flow through the venturi section 72 is reduced, and thus, the supply pressure of the second fluid supply 28 is increased. If the distal end 74 of the outlet conduit 46 is moved further out of the venturi section 72 (i.e., back towards the component feed system 40), the area for the second fluid supply 28 to flow through the venturi section 72 is increased, and thus, the supply pressure of the second fluid supply 28 entering the first mixing junction 56 is decreased as is the vacuum level on the component feed system 40. In some embodiments, it is preferable to control the pressure difference between the second fluid pressure prior to the first mixing junction 56 and the discharge pressure to be less than or equal to 25 pounds per square inch (psi), or more preferably, less than 20 psi, or less than 15 psi, or less than 10 psi, or less than 5 psi.

Another feature of the first mixing junction 56 that can create enhanced mixing and transfer of the supply of the component 44 into the second fluid supply 28 in the first mixing junction 56 can be that the second inlet 62 providing the second fluid supply 28 is upstream of the distal end 74 of the outlet conduit 46 that provides the supply of the component 44 from the component feed system 40 to the first mixing junction 56. With such a configuration, the second fluid supply 28 can enter the first mixing junction 56 upstream of the supply of the component 44 to prevent any of the supply of the component 44 from engaging or sticking on an internal surface of the first mixing junction 56. Thus, in the embodiment depicted in FIG. 3, the co-axial nature of the outlet axis 68 of the outlet conduit 46 and the discharge axis 70 of the first mixing junction 56 and the upstream entry of the second fluid supply 28 into the first mixing junction 56 can create an annular-shaped fluid protection around the entry of the supply of the component 44 as it is entrained in the second fluid supply 28 in the first mixing junction 56.

It is to be noted that while a single outlet conduit 46 of the component feed system 40 and a single first mixing junction 56 is illustrated in FIGS. 1-3, it is contemplated that the outlet conduit 46 can be split into two or more conduits to feed two or more first mixing junctions 56 for mixing the supply of the component 44 with the second fluid supply 28. In such a configuration, the second fluid supply 28 can include as many conduits as there are first mixing junctions 56. By having more than one outlet conduit 46 and more than one first mixing junction 56 to mix the supply of the component 44 with the second fluid supply 28, a greater flow rate of the second fluid supply 28 including the component from the supply of the component 44 can be achieved.

In some embodiments, it is also contemplated that the first mixing junction 56 can be an eductor of different configuration other than a co-axial eductor as described above. For example, it is contemplated that the first mixing junction 56 can be an eductor that is shaped as a slot eductor.

Referring back to FIG. 1, the apparatus 10 can include a second mixing junction 58 in some embodiments. The second mixing junction 58 can provide the functionality of mixing the second fluid supply 28 including the component from the supply of the component 44 with the first fluid supply 16. As the second fluid supply 28 including the component from the supply of the component 44 exits the discharge 64 of the first mixing junction 56 it can be transferred to the second mixing junction 58. The first fluid supply 16 can be delivered to the second mixing junction 58 by the first pump 36. The second mixing junction 58 can mix the first fluid supply 16 and any of its components (e.g., fluid 18, fibers 20, surfactant 22) with the second fluid supply 28 and any of its components (e.g., fluid 30, surfactant 32) and the component from the supply of the component 44 to provide a resultant slurry 76. The resultant slurry 76 can be transferred from the second mixing junction 58 through a discharge 78 of the second mixing junction 58 and to a headbox 80. In some embodiments, there can be a separation between the discharge 78 of the second mixing junction 58 and the headbox 80, as depicted in FIG. 3. However, in other embodiments, the discharge 78 of the second mixing junction 58 can be integral with the headbox 80.

Figure 4A:
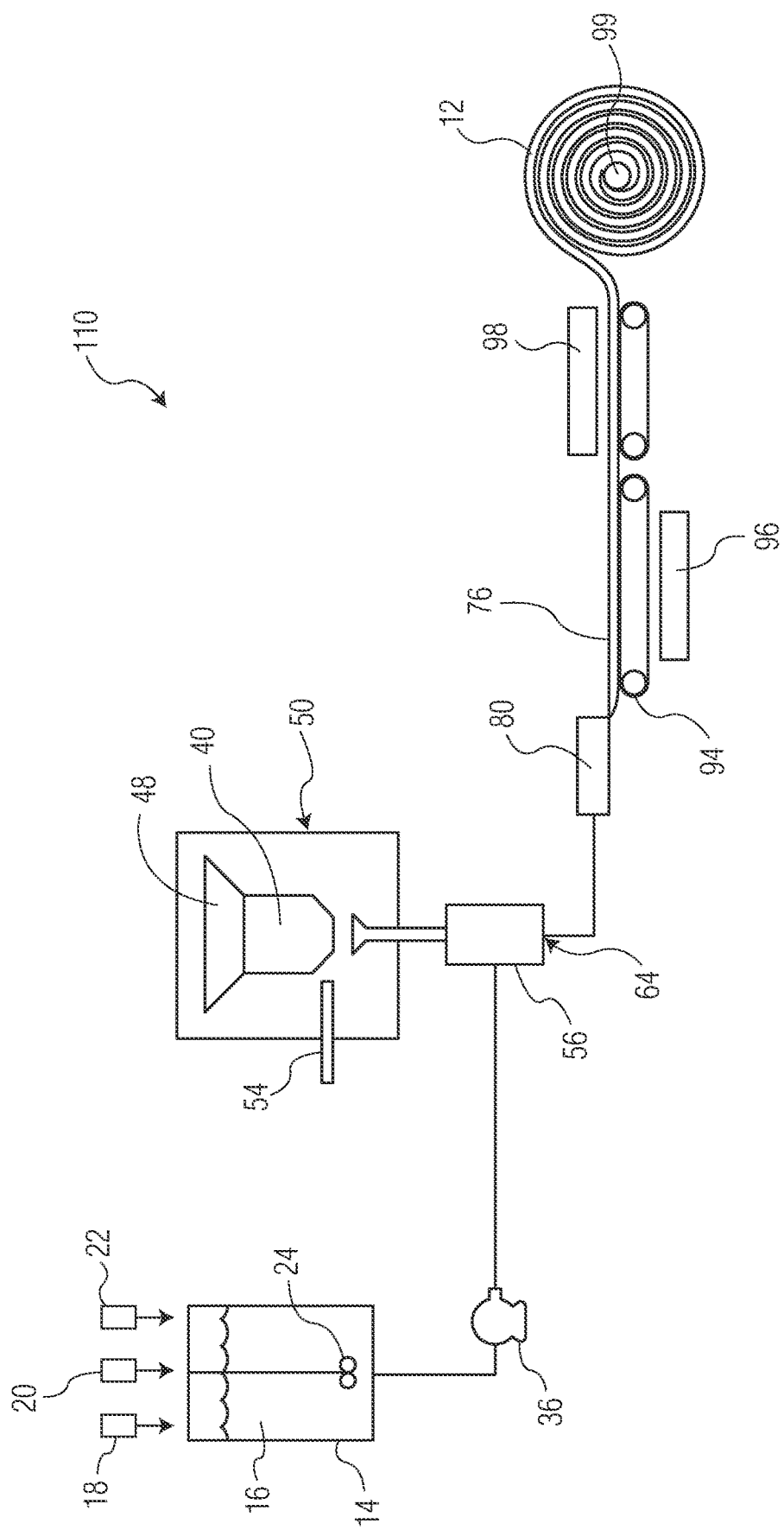
FIG. 4A is a process schematic of an alternative exemplary method for introducing a component into a fluid supply and forming a substrate including a component according to another embodiment of the present disclosure.

An alternative embodiment of an apparatus 110 and method of forming a substrate 12 is depicted in FIG. 4A. FIG. 4A has the same components as the apparatus 10 and method as described in FIGS. 1-3 unless noted herein. The apparatus 110 of FIG. 4A only includes a first tank 14 for holding a first fluid supply 16. The apparatus 110 and method of FIG. 4A does not include a second tank 26 including a second fluid supply 28. The first fluid supply 16 can include a supply of fluid 18, a supply of fibers 20, and a supply of surfactant 22. The apparatus 110 can also include a component feed system 40, a fluid control system 50, and a mixing junction 56 as described above with respect to FIGS. 1-3. Based on this configuration, the first pump 36 can transfer the first fluid supply 16 to the first mixing junction 56. The component feed system 40 can transfer a supply of component 44 to the first mixing junction 56 as previously described. In preferred embodiments, the first mixing junction 56 can be an eductor, and more preferably, a co-axial eductor as described with respect to FIG. 3. The first mixing junction 56 can mix the first fluid supply 16 with component from the supply of the component 44 and provide a resultant slurry 76 that exits the discharge 64 of the first mixing junction 56 and is transferred to the headbox 80. In some embodiments, the discharge 64 of the first mixing junction 56 can be separate from the headbox 80, however, in some embodiments, the discharge 64 of the first mixing junction 56 can be integral to the headbox 80. In some embodiments, the first fluid supply 16 can include fluid 18 and surfactant 22 to be mixed with the supply of the component 44 to provide the resultant slurry 76, but be free from any fibers. In other embodiments, the first fluid supply 16 can include fluid 18, fibers 20, and surfactant 22 to be mixed with the supply of the component 44 to provide the resultant slurry 76.

Figure 4B:
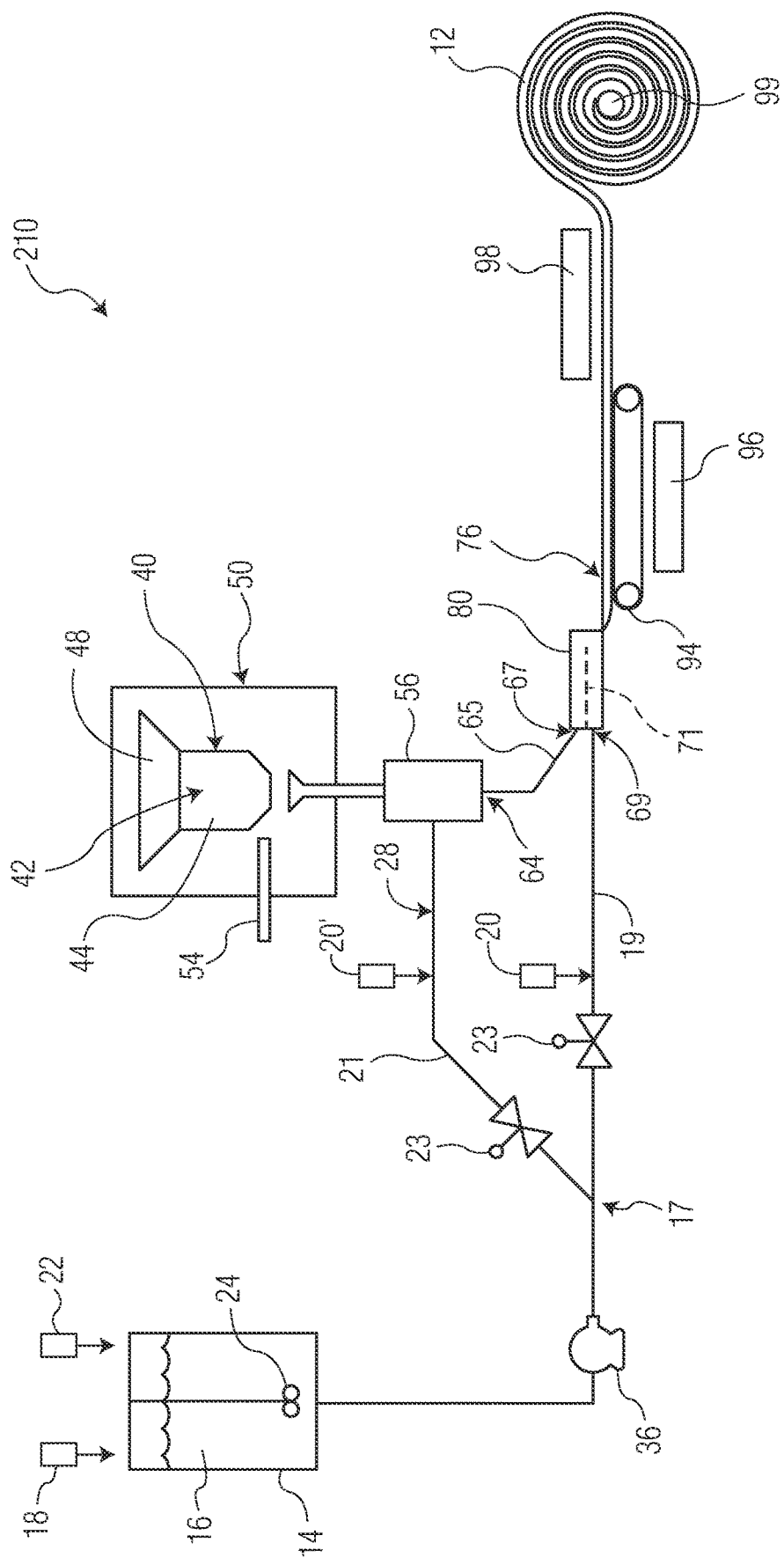
FIG. 4B is a process schematic of another alternative exemplary method for introducing a component into a fluid supply and forming a substrate including a component according to another embodiment of the present disclosure.

Another alternative embodiment of an apparatus 210 and method for forming a substrate 12 is depicted in FIG. 4B. The apparatus 10 can include a first pump 36 that can be in fluid communication with the first fluid supply 16. The first fluid supply 16 can include a supply of the fluid 18 and surfactant 22. The first fluid supply 16 can be split at junction 17. The first fluid supply 16 can continue past two control valves 23. The first fluid supply 16 can continue past one of the control valves 23 in conduit 19 and towards headbox 80. A supply of fibers 20 can be added to the first fluid supply 16 past the control valve 23. Preferably, the supply of fibers 20 can be provided to the first fluid supply 16 in a supply of fluid, such as a foam.

When the first fluid supply is split at junction 17, the first fluid supply 16 can be pumped past a second control valve 23 in conduit 21 towards the first mixing junction 56. The fluid supply in this conduit can be referred to as the second fluid supply 28. The second fluid supply 28 can include a supply of fluid 18 and surfactant 22 (that is from the first fluid supply 16). In some embodiments, it may be preferable to add a supply of fibers 20' to the second fluid supply 28, as illustrated in FIG. 4B. Preferably, the supply of fibers 20' can be provided to the first fluid supply 16 in a supply of fluid, such as a foam.

In the embodiment depicted in FIG. 4B, the supply of the component 44 can be added to the second fluid supply 28 at the first mixing junction 56 as describe above. The apparatus 210 can include an output 65 of the first mixing junction 56 including the component 44 downstream of the discharge 64 of the first mixing junction 64. The supply of fluid and component 44 in the output 65 of the first mixing junction 56 can provide a first input 67 into the headbox 80. The first fluid supply 16 can provide a second input 69 into the headbox 80. The first input 67 can be separate from the second input 69 into the headbox 80. For example, in some embodiments, the first input 67 including the component 44 can be separated from the second input 69 by a z-directional divider 71 (also referred to as a lamellae), and thus, the fluid supplies 16, 28 can be separated from one another for at least a portion of the headbox 80 as the fluid supplied 16, 28 are transferred through the headbox 80 to provide the resultant slurry 76. In doing so, the resultant slurry 76 can provide two different layers to provide a two-layered substrate 12.

Figure 4C:
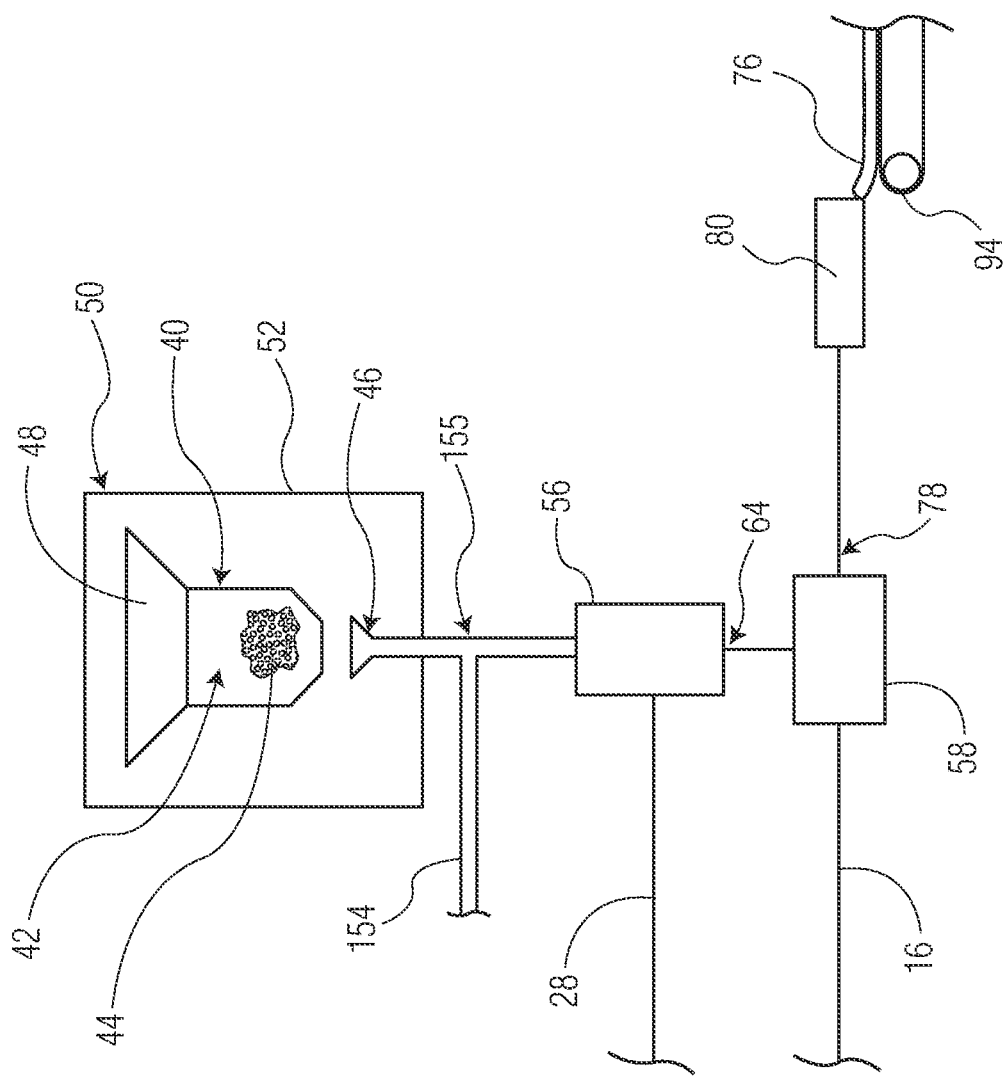
FIG. 4C is a process schematic of another alternative exemplary method for introducing a component into a fluid supply and forming a substrate including a component according to another embodiment of the present disclosure.

Yet another alternative embodiment is illustrated in FIG. 4C. FIG. 4C is similar to the configuration depicted in FIG. 2, however, a bleed-in orifice 154 is provided in the configuration of FIG. 4C that can provide controlled fluid flow to the supply of the component 44 after the component 44 enters the outlet conduit 46 of the component feed system 40, but upstream of the first mixing junction 56. Such a configuration can provide fluid (e.g., liquid, gas, or foam) to the supply of the component 44 to help control the entrainment of fluid within the second fluid supply 28 as the supply of the component 44 is mixed with the second fluid supply 28 in the first mixing junction 56. For example, in one embodiment, adding a flow of foam in the bleed-in orifice 154 can help prevent additional gas (e.g., air) from entraining in the supply of the component 44 as it is mixed with the second fluid supply 28.

Regardless of whether the apparatus 10, 110, 210 and method used for transferring the resultant slurry 76 is as described herein, or is another apparatus and/or method, a headbox 80 can be provided to further transfer the resultant slurry 76 to form a substrate 12. As depicted in FIGS. 5-9, the headbox 80 can have a machine direction 81 and a cross direction 83. The machine direction 81 is in the direction of the transfer of the resultant slurry 76 through the headbox 80. The resultant slurry 76 is not shown in FIGS. 5-9 for clarity purposes.

Figure 5:
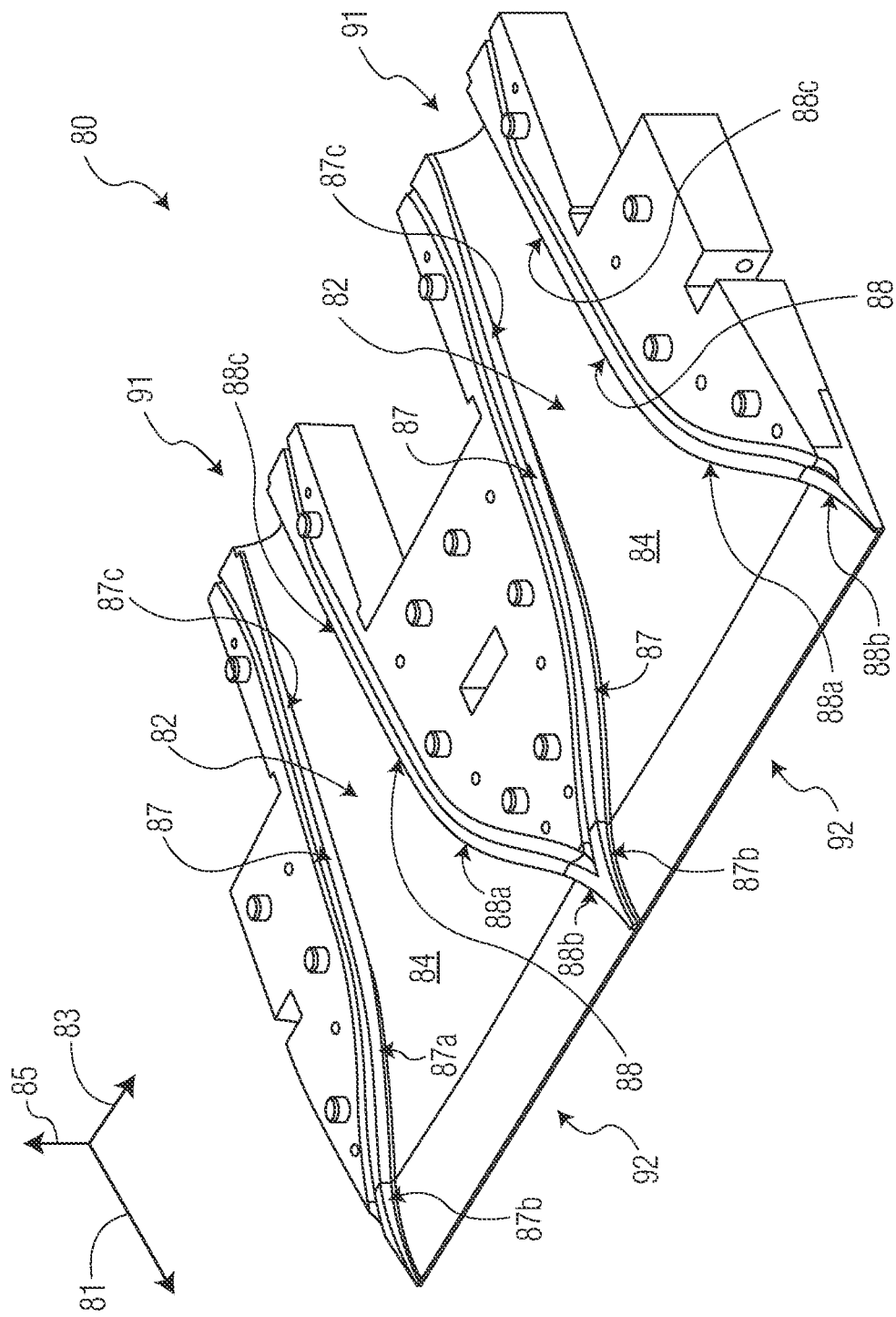
FIG. 5 is a front, top, perspective view of an exemplary headbox, with the top surface being removed for purposes of clarity.

The headbox 80 can include at least one flow section 82. In the embodiment of the headbox 80 depicted in FIGS. 5-9, the headbox 80 includes two flow sections 82. As illustrated in FIG. 5, the flow sections 82 can be spaced apart from one another in the cross direction 83, but can be in the same general plane defined by the machine direction 81 and the cross direction 83. It is contemplated that in some embodiments including more than one flow section 82, the flow sections 82 could be arranged such that one flow section 82 is disposed on top of the other flow section 82 in a z-direction 85 perpendicular to the plane defined by the machine direction 81 and the cross direction 83. In some embodiments including more than one flow section 82, the two flow section 82 can be configured substantially similar to one another. However, it is also contemplated that one flow section 82 could be configured differently from the other flow section 82 depending on various factors, such as, but not limited to the characteristics of the substrate 12 desired to be formed. Additionally, although two flow sections 82 are shown in the embodiment of FIGS. 5-9, it is contemplated that a headbox 80 can include three or more flow sections 82. The number of flow sections 82 can be adjusted to accomplish various flow rates of the resultant slurry 76, desired width of the substrate 12, and/or the number of z-directional layers of the substrate 12.

Figure 6:
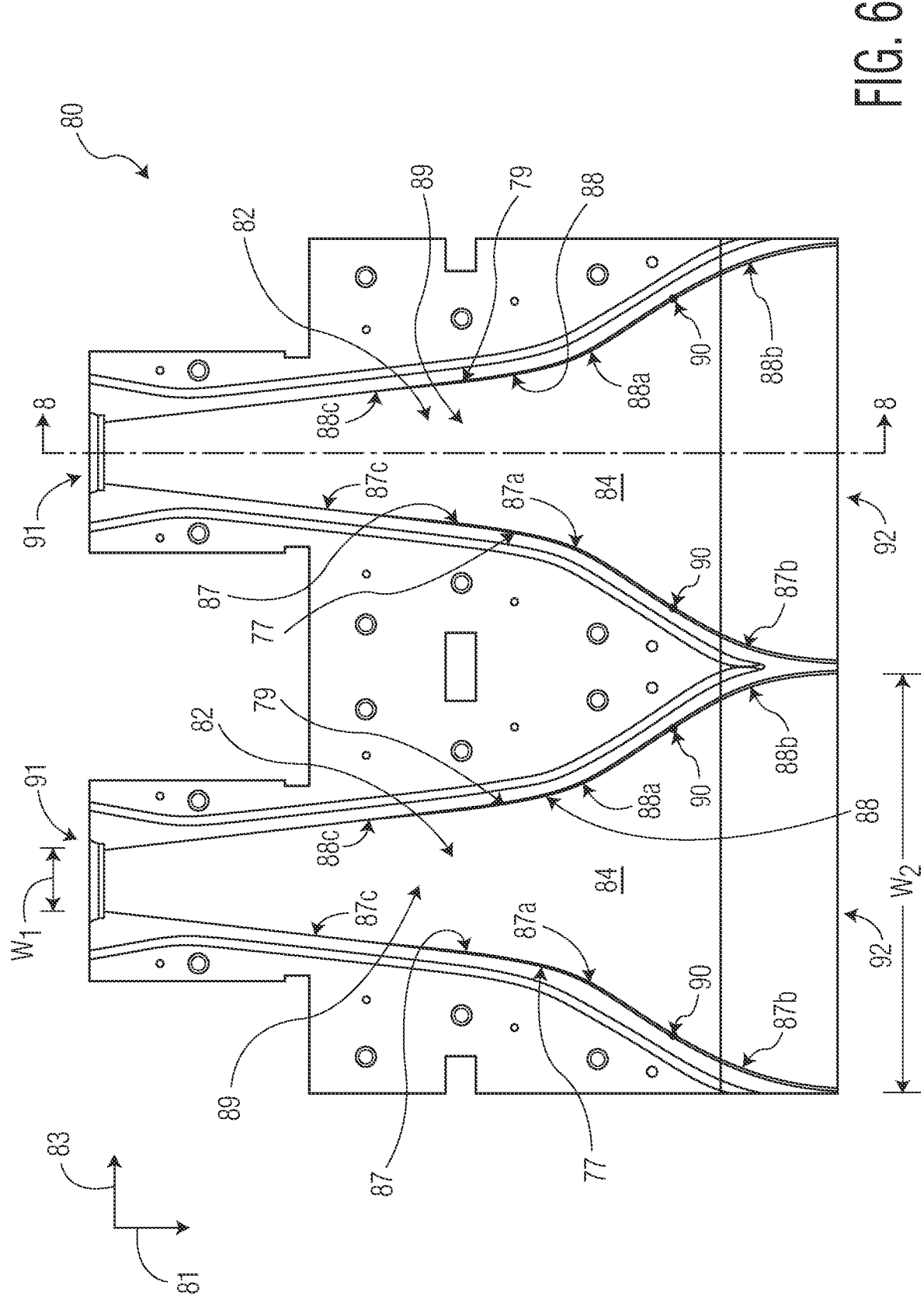
FIG. 6 is a top plan view of the headbox of FIG. 5.
Figure 7:
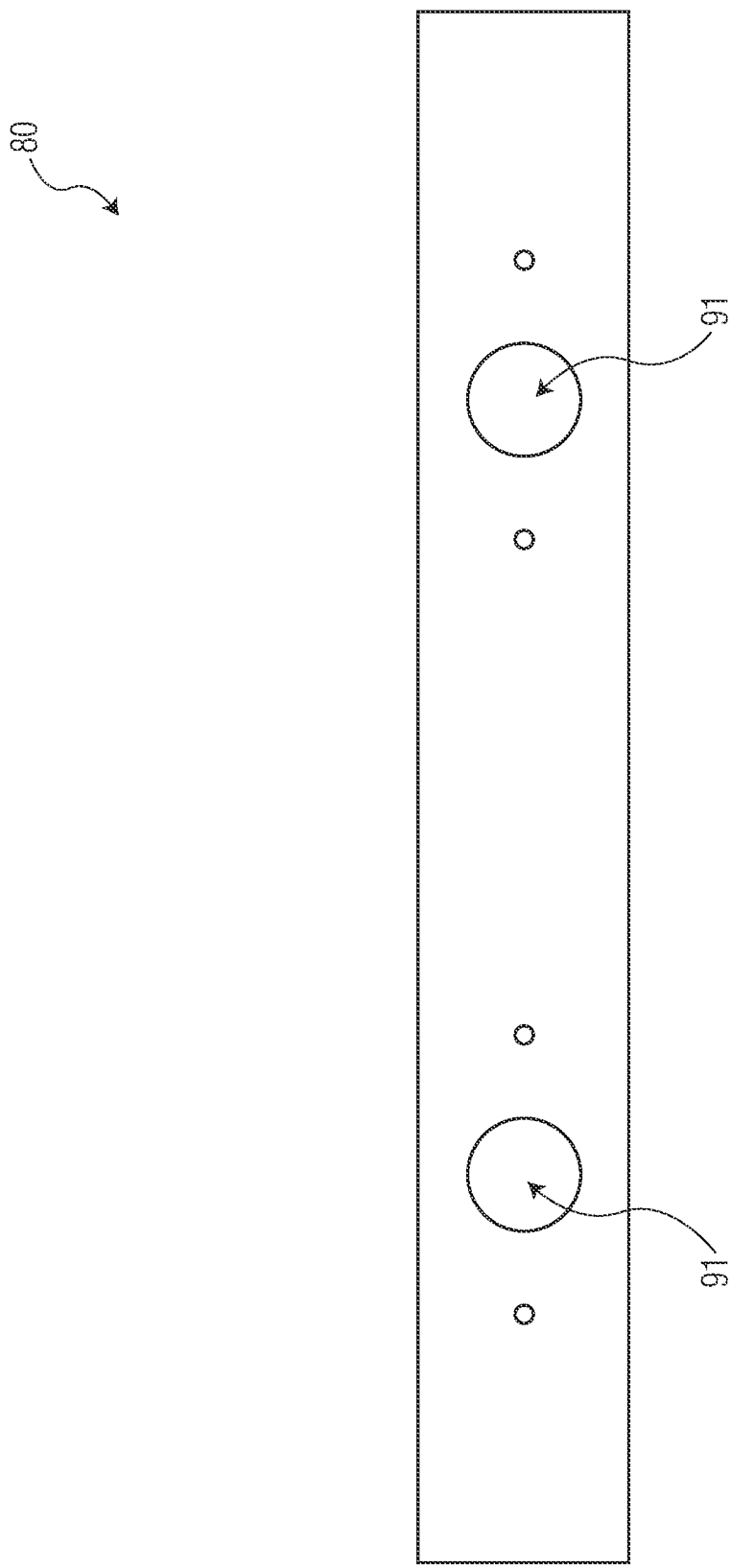
FIG. 7 is a back plan view of the headbox of FIG. 5.
Figure 8:
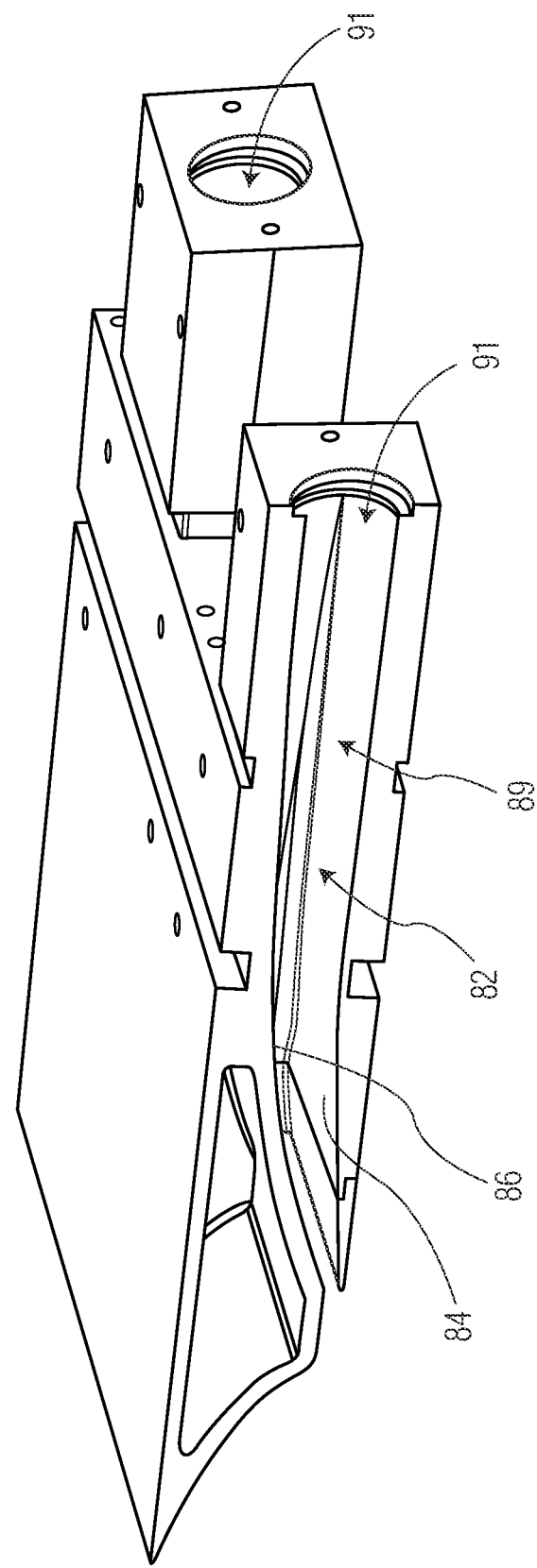
FIG. 8 is a side, top, perspective, cross-section view taken along line 8-8 from FIG. 6, with the top surface being shown.
Figure 9:
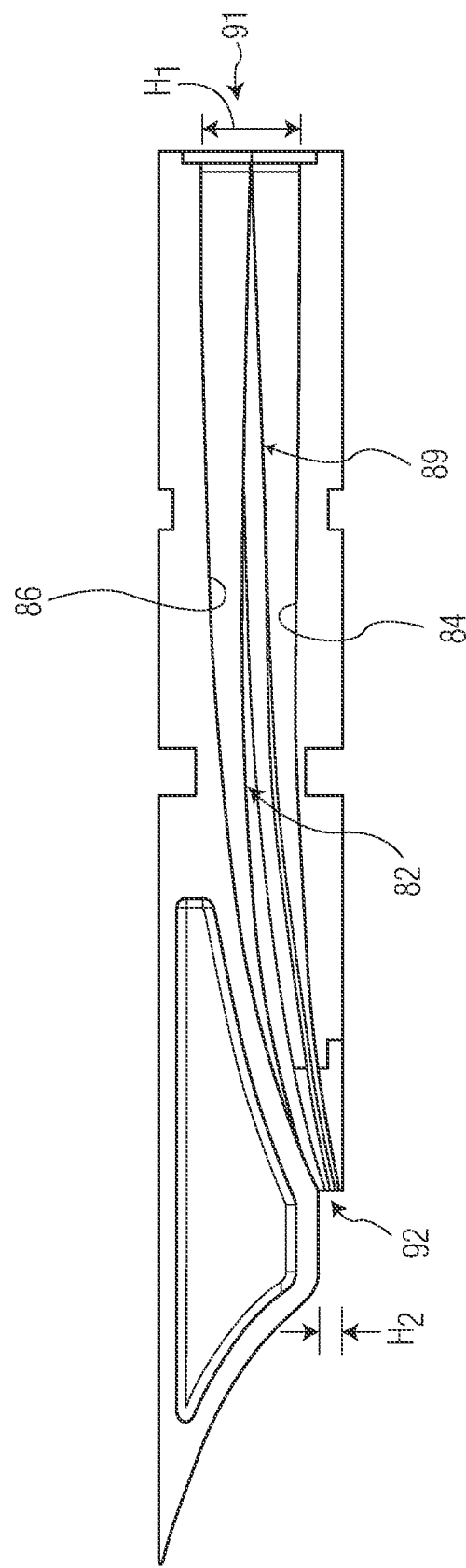
FIG. 9 is a side, cross-section view taken along line 8-8 from FIG. 6, with the top surface being shown.

Each flow section 82 can include a bottom surface 84 and a top surface 86 (labeled in FIGS. 8 and 9). The top surface 86 is removed from FIGS. 5-7 for clarity purposes of depicting the internal features of the headbox 80. The flow section 82 can also include a first side 87 and a second side 88. The second side 88 can be opposite from the first side 87. In some embodiments, the first side 87 and the second side 88 can be configured to be symmetric to one another about an axis parallel to the machine direction 81. As best depicted in FIG. 6, the first side 87 and the second side 88 can include a first portion 87a, 88a, respectively, that are convex to an interior 89 of the flow section 82. The first side 87 and the second side 88 can also include a second portion 87b, 88b, respectively, that are concave to the interior 89 of the flow section 82. In some embodiments, the first side 87 and the second side 88 can each include a changing radius of curvature along a length of the first portion 87a and the second portion 88b in the machine direction 81. The first side 87 and the second side 88 can be configured such that each side 87, 88 includes an inflection segment 90. The inflection segment 90 can serve as the transition between the first portion 87a, 88a and the second portion 87b, 88b of the first and second sides 87, 88, respectively. The inflection segment 90 can be a linear segment, or can be more abrupt, such as depicted in FIGS. 5 and 6 (in which the inflection segment 90 is noted with a dot for identification purposes).

The interior 89 can include a machine directional side profile when viewed from a top-down view of the interior 89, such as depicted in FIG. 6, that includes a first side profile 77 and a second side profile 79. The first side profile 77 can be a profile of the first side 87 and the second side profile 79 can be a profile of the second side 88 as viewed from a top-down view of the interior 89. The first side profile 77 and the second side profile 79 can each include a first portion 87*a*, 88*a*, respectively, that are convex to the interior 89 of the flow section 82 and each include a second portion 87*b*, 88*b*, respectively, that are concave to the interior 89 of the flow section 82. For example, these side profiles 77, 79 can be obtained whether there is a first side 87, second side 88, top surface 86, and bottom surface 84, or whether such sides 87, 88 and top and bottom surface 86, 84 are not clearly demarcated, such as if the interior 89 of the flow section 82 is defined by smooth surfaces and curvatures, such as in a cross-section that is oval in shape.

The headbox 80 can be configured such that each flow section 82 includes an inlet 91. Each flow section 82 can also include an outlet 92. As illustrated in the rear view of the headbox 80 in FIG. 7, in some embodiments, the inlet 91 can be circular in a cross-sectional shape, such that it can connect to a circular cross-section conduit that transfers the resultant slurry 76 to the headbox 80. Of course, it is contemplated that the inlet 91 can have other cross-sectional shapes. Additionally, it is also contemplated that the inlet 91 of the headbox 80 can form a part of the discharge 78 of the second mixing junction 58 or the first mixing junction 56 discussed above.

As shown for the left flow section 82 in FIG. 6, the width $W_1$ of the interior 89 at the inlet 91 can be less than the width $W_2$ of the interior 89 at the outlet 92. For purposes herein, the widths $W_1$ and $W_2$ are defined as being measured between the first side 87 and the second side 88 in a direction parallel to the cross direction 83 of the headbox 80 and in the plane defined by the machine direction 81 and the cross direction 83.

As depicted in FIG. 9, the interior 89 of the flow section 82 can include a height $H_1$ of at the inlet 91 that is greater than a height $H_2$ of the interior 89 at the outlet 92. For purposes herein, the heights $H_1$ and $H_2$ are defined as being measured between the bottom surface 84 and the top surface 86 in a direction parallel to the z-direction 85 that is perpendicular to the plane defined by the machine direction 81 and the cross direction 83. Also depicted in FIG. 9, the interior 89 of the flow section 82 is constructed such that the top surface 86 and the bottom surface 84 provide a change in the flow path between the inlet 91 and the outlet 92 in the z-direction 85.

In some embodiments, the first side 87 and the second side 88 of the flow section 82 can each include a flow spreading portion 87*c*, 88*c*, respectively. The flow spreading portion 87*c*, 88*c* can be closer to the inlet 91 than is the first portion 87*a*, 88*a* of the first side 87 and the second side 88, respectively. The first portion 87*a*, 88*a* of the first side 87 and the second side 88, respectively, can be closer to the inlet 91 than is the second portion 87*b*, 88*b* of the first side 87 and the second side 88, respectively.

When the resultant slurry 76 enters the headbox 80 through each inlet 91, the resultant slurry 76 first enters the interior 89 of the flow section 82 and the flow spreading portions 87*c*, 88*c* of the first side 87 and the second side 88, respectively. While here, the flow path of the resultant slurry 76 increases in its width in the cross direction 83. After passing through flow spreading portions 87*c*, 88*c* of the first side 87 and the second 88, respectively, the resultant slurry 76 expands more substantially in width as it transfers by the first portions 87*a*, 88*a* of the first and second sides 87, 88, respectively. The flow of the resultant slurry 76 then passes the inflection segment 90 of on each of the first and second sides 87, 88 and finally transfers by the second portions 87*b*, 88*b* of the first and second sides 87, 88, respectively. Importantly, this controlled expansion in width of the flow of the resultant slurry 76 and the combination of the first portions 87*a*, 88*a* and second portions 87*b*, 88*b* of the first and second sides 87, 88, respectively, provides for improved flow throughout the interior 89 of the flow section 82 that reduces eddies or other turbulent properties of the resultant slurry 76 as it passes through the headbox 80. Thus, the side profiles 77, 79 of the interior 89 of the flow section 89 (e.g., the first and second sides 87, 88) create a configuration that is beneficial to minimizing the time the resultant slurry 76 is in the headbox 80 while expanding to a desired width and height for forming the substrate 12. This can be a significant processing advantage where components from the supply of the component 44 are dry items, such as SAM, for which it is desirable to minimize exposure time to liquids that form part of the resultant slurry 76.

Additionally, the configuration of the changing height and width of the interior 89 of the flow section 82 is believed to assist in providing enhanced flow consistency for the resultant slurry 76 through the headbox 80. As described above, the width $W_1$ of the interior 89 at the inlet 91 is less than the width $W_2$ of interior 89 at the outlet 92 to allow for the resultant slurry 76 to spread out in the cross direction 83 to a desired width of the substrate 12. As the width of the interior 89 is increasing as the resultant slurry 76 passes through the headbox 80, the height of the interior 89 is decreasing. As noted above, the height $H_1$ of the interior 89 at the inlet 91 is greater than a height $H_2$ of the interior 89 of the flow section 82 at the outlet 92. By decreasing the height of the interior 89 as the width increases 89, the flow of the resultant slurry 76 through the interior 89 of the headbox 80 is maintained in a more laminar fashion. Again, this helps to reduce the time the resultant slurry 76 is in the headbox 80, which as noted above, can be advantageous when the resultant slurry 76 includes components from the supply of the component 44 for dry items, such as SAM, for which it is desirable to minimize exposure time to liquids.

Also of note, it is believed that the arcing shape in the z-direction 85 between the top surface 86 and the bottom surface 84 between the inlet 91 and the outlet 92 provide enhanced control of the flow of the resultant slurry 76 and can help reduce eddies, or other turbulence of the flow of the resultant slurry 76 through the headbox 80, further adding to the advantages noted above with respect to the components from the supply of the component 44. For example, it is believed that this arcing shape can provide a more consistent basis weight and fiber orientation across the cross direction 83 in the substrate 12 that is formed, particularly when used in a foam forming process.

Referring back to FIGS. 1 and 4, the apparatus 10, 110, 210 can also include a forming surface 94 onto which the resultant slurry 76 is deposited after exiting the outlet 92 of the headbox 80. The forming surface 94 can be a foraminous sheet, such as a woven belt or screen, or any other suitable surface for accepting the resultant slurry 76. In some embodiments, the resultant slurry 76 may be deposited onto another pre-formed substrate that may be on top of the forming surface 94. The apparatus 10, 110 can also include a dewatering system 96 that can be configured to remove liquid from the resultant slurry 76 on the forming surface 94. In some embodiments, the dewatering system 96 can be configured to provide a vacuum to the resultant slurry 76 to pull liquid from the resultant slurry 76, and in doing so, can turn the resultant slurry 76 including the plurality of fibers 20 and the component 44 into a substrate 12. In some embodiments, the apparatus 10, 110, 210 can also include a drying system 98. The drying system 98 can be configured to further dry the resultant slurry 76 and/or the substrate 12. In some embodiments, the apparatus 10, 110, 210 can include a winding system 99 that can be configured to wind the substrate 12 in a roll fashion. In other embodiments, the apparatus 10, 110, 210 can festoon the substrate 12, or collect the substrate 12 in any other suitable configuration.

Foaming Fluid

The foam forming processes as described herein can include a foaming fluid. In some embodiments, the foaming fluid can comprise between about 85% to about 99.99% of the foam (by weight). In some embodiments, the foaming fluid used to make the foam can comprise at least about 85% of the foam (by weight). In certain embodiments, the foaming fluid can comprise between about 90% and about 99.9% of the foam (by weight). In certain other embodiments, the foaming fluid can comprise between about 93% and 99.5% of the foam or even between about 95% and about 99.0% of the foam (by weight). In preferred embodiments, the foaming fluid can be water, however, it is contemplated that other processes may utilize other foaming fluids.

Foaming Surfactant

The foam forming processes as described herein can utilize one of more surfactants. The fibers and surfactant, together with the foaming liquid and any additional components, can form a stable dispersion capable of substantially retaining a high degree of porosity for longer than the drying process. In this regard, the surfactant is selected so as to provide a foam having a foam half life of at least 2 minutes, more desirably at least 5 minutes, and most desirably at least 10 minutes. A foam half life can be a function of surfactant types, surfactant concentrations, foam compositions/solid level and mixing power/air content in a foam. The foaming surfactant used in the foam can be selected from one or more known in the art that are capable of providing the desired degree of foam stability. In this regard, the foaming surfactant can be selected from anionic, cationic, nonionic and amphoteric surfactants provided they, alone or in combination with other components, provide the necessary foam stability, or foam half life. As will be appreciated, more than one surfactant can be used, including different types of surfactants, as long as they are compatible, and more than one surfactant of the same type. For example, a combination of a cationic surfactant and a nonionic surfactant or a combination of an anionic surfactant and a nonionic surfactant may be used in some embodiments due to their compatibilities. However, in some embodiments, a combination of a cationic surfactant and an anionic surfactant may not be satisfactory to combine due to incompatibilities between the surfactants.

Anionic surfactants believed suitable for use with the present disclosure include, without limitation, anionic sulfate surfactants, alkyl ether sulfonates, alkylaryl sulfonates, or mixtures or combinations thereof. Examples of alkylaryl sulfonates include, without limitation, alkyl benzene sulfonic acids and their salts, dialkylbenzene disulfonic acids and their salts, dialkylbenzene sulfonic acids and their salts, alkylphenol sulfonic acids/condensed alkylphenol sulfonic acids and their salts, or mixture or combinations thereof. Examples of additional anionic surfactants believed suitable for use in the present disclosure include alkali metal sulforicinates, sulfonated glyceryl esters of fatty acids such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles such as palmitonitrile sulfonate, alkali metal alkyl sulfates such as sodium lauryl sulfate, ammonium lauryl sulfate or triethanolamine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, sulphuric esters of polyoxyethylene alkyl ether, sodium salts, potassium salts, and amine salts of alkylnapthylsulfonic acid. Certain phosphate surfactants including phosphate esters such as sodium lauryl phosphate esters or those available from the Dow Chemical Company under the tradename TRITON are also believed suitable for use herewith. A particularly desired anionic surfactant is sodium dodecyl sulfate (SDS).

Cationic surfactants are also believed suitable for use with the present disclosure for manufacturing some embodiments of substrates. In some embodiments, such as those including superabsorbent material, cationic surfactants may be less preferable to use due to potential interaction between the cationic surfactant(s) and the superabsorbent material, which may be anionic. Foaming cationic surfactants include, without limitation, monocarbyl ammonium salts, dicarbyl ammonium salts, tricarbyl ammonium salts, monocarbyl phosphonium salts, dicarbyl phosphonium salts, tricarbyl phosphonium salts, carbylcarboxy salts, quaternary ammonium salts, imidazolines, ethoxylated amines, quaternary phospholipids and so forth. Examples of additional cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethylstearylamide, and amine salts of long chain fatty acids. Further examples of cationic surfactants believed suitable for use with the present disclosure include benzalkonium chloride, benzethonium chloride, cetrimonium bromide, distearyldimethylammonium chloride, tetramethylammonium hydroxide, and so forth.

Nonionic surfactants believed suitable for use in the present disclosure include, without limitation, condensates of ethylene oxide with a long chain fatty alcohol or fatty acid, condensates of ethylene oxide with an amine or an amide, condensation products of ethylene and propylene oxides, fatty acid alkylol amide and fatty amine oxides. Various additional examples of non-ionic surfactants include stearyl alcohol, sorbitan monostearate, octyl glucoside, octaethylene glycol monododecyl ether, lauryl glucoside, cetyl alcohol, cocamide MEA, monolaurin, polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol, alkylpolysaccharides, polyethylene glycol sorbitan monooleate, octylphenol ethylene oxide, and so forth.

The foaming surfactant can be used in varying amounts as necessary to achieve the desired foam stability and air-content in the foam. In certain embodiments, the foaming surfactant can comprise between about 0.005% and about 5% of the foam (by weight). In certain embodiments the foaming surfactant can comprise between about 0.05% and about 3% of the foam or even between about 0.05% and about 2% of the foam (by weight).

Fibers

As noted above, the apparatus 10, 110 and methods described herein can include providing a fibers from a supply of fibers 18. In some embodiments, the fibers can be suspending in a fluid supply 16, 28 that can be a foam. The foam suspension of fibers can provide one or more supply of fibers. In some embodiments, the fibers utilized herein can include natural fibers and/or synthetic fibers. In some embodiments, a fiber supply 18 can include only natural fibers or only synthetic fibers. In other embodiments, a fiber supply 18 can include a mixture of natural fibers and synthetic fibers. Some fibers being utilized herein can be absorbent, whereas other fibers utilized herein can be non-absorbent. Non-absorbent fibers can provide features for the substrates that are formed from the methods and apparatuses described herein, such as improved intake or distribution of fluids.

A wide variety of cellulosic fibers are believed suitable for use herein. In some embodiments, the fibers utilized can be conventional papermaking fibers such as wood pulp fibers formed by a variety of pulping processes, such as kraft pulp, sulfite pulp, bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), and so forth. By way of example only, fibers and methods of making wood pulp fibers are disclosed in U.S. Pat. No. 4,793,898 to Laamanen et al.; U.S. Pat. No. 4,594,130 to Chang et al.; U.S. Pat. No. 3,585,104 to Kleinhart; U.S. Pat. No. 5,595,628 to Gordon et al.; U.S. Pat. No. 5,522,967 to Shet; and so forth. Further, the fibers may be any high-average fiber length wood pulp, low-average fiber length wood pulp, or mixtures of the same. Examples of suitable high-average length pulp fibers include softwood fibers, such as, but not limited to, northern softwood, southern softwood, redwood, red cedar, hemlock, pine (e.g., southern pines), spruce (e.g., black spruce), and the like. Examples of suitable low-average length pulp fibers include hardwood fibers, such as, but not limited to, eucalyptus, maple, birch, aspen, and the like.

Moreover, if desired, secondary fibers obtained from recycled materials may be used, such as fiber pulp from sources such as, for example, newsprint, reclaimed paperboard, and office waste. In a particularly preferred embodiment refined fibers are utilized in the tissue web such that the total amount of virgin and/or high average fiber length wood fibers, such as softwood fibers, may be reduced.

Regardless of the origin of the wood pulp fiber, the wood pulp fibers preferably have an average fiber length greater than about 0.2 mm and less than about 3 mm, such as from about 0.35 mm and about 2.5 mm, or between about 0.5 mm to about 2 mm or even between about 0.7 mm and about 1.5 mm.

In addition, other cellulosic fibers that can be used in the present disclosure includes nonwoody fibers. As used herein, the term "non-wood fiber" generally refers to cellulosic fibers derived from non-woody monocotyledonous or dicotyledonous plant stems. Non-limiting examples of dicotyledonous plants that may be used to yield non-wood fiber include kenaf, jute, flax, ramie and hemp. Non-limiting examples of monocotyledonous plants that may be used to yield non-wood fiber include cereal straws (wheat, rye, barley, oat, etc.), stalks (corn, cotton, sorghum, *Hesperaloe funifera*, etc.), canes (bamboo, sisal, bagasse, etc.) and grasses (miscanthus. esparto, lemon, sabai, switchgrass, etc). In still other certain instances non-wood fiber may be derived from aquatic plants such as water hyacinth, microalgae such as *Spirulina*, and macroalgae seaweeds such as red or brown algae.

Still further, other cellulosic fibers for making substrates herein can include synthetic cellulose fiber types formed by spinning, including rayon in all its varieties, and other fibers derived from viscose or chemically-modified cellulose such as, for example, those available under the trade names LYOCELL and TENCEL.

In some embodiments, the non-woody and synthetic cellulosic fibers can have fiber length greater than about 0.2 mm including, for example, having an average fiber size between about 0.5 mm and about 50 mm or between about 0.75 and about 30 mm or even between about 1 mm and about 25 mm. Generally speaking, when fibers of relatively larger average length are being used, it may often be advantageous to modify the amount and type of foaming surfactant. For example, in some embodiments, if fibers of relatively larger average length are being used, it may be beneficial to utilize relatively higher amounts of foaming surfactant in order to help achieve a foam with the required foam half life.

Additional fibers that may be utilized in the present disclosure include fibers that are resistant to the forming fluid, namely those that are non-absorbent and whose bending stiffness is substantially unimpacted by the presence of forming fluid. As noted above, typically the forming fluid will comprise water. By way of non-limiting example, water-resistant fibers include fibers such as polymeric fibers comprising polyolefin, polyester (PET), polyamide, polylactic acid, or other fiber forming polymers. Polyolefin fibers, such as polyethylene (PE) and polypropylene (PP), are particularly well suited for use in the present disclosure. In some embodiments, non-absorbent fibers can be recycled fibers, compostable fibers, and/or marine degradable fibers. In addition, highly cross-linked cellulosic fibers having no-significant absorbent properties can also be used herein. In this regard, due to its very low levels of absorbency to water, water resistant fibers do not experience a significant change in bending stiffness upon contacting an aqueous fluid and therefore are capable of maintain an open composite structure upon wetting. The fiber diameter of a fiber can contribute to enhanced bending stiffness. For example, a PET fiber has a higher bending stiffness than a polyolefin fiber whether in dry or wet states. The higher the fiber denier, the higher the bending stiffness a fiber exhibits. Water resistant fibers desirably have a water retention value (WRV) less than about 1 and still more desirably between about 0 and about 0.5. In certain aspects, it is desirable that the fibers, or at least a portion thereof, include non-absorbent fibers.

The synthetic and/or water resistant fibers can have fiber length greater than about 0.2 mm including, for example, having an average fiber size between about 0.5 mm and about 50 mm or between about 0.75 and about 30 mm or even between about 1 mm and about 25 mm.

In some embodiments, the synthetic and/or water resistant fibers can have a crimped structure to enhance bulk generation capability of the foam formed fibrous substrate. For example, a PET crimped staple fiber may be able to generate a higher caliper (or result in a low sheet density) in comparison to a PET straight staple fiber with the same fiber diameter and fiber length.

In some embodiments, the total content of fibers, can comprise between about 0.01% to about 10% of the foam (by weight), and in some embodiments between about 0.1% to about 5% of the foam (by weight).

Binder

In some embodiments, a fluid supply 16, 28 can include binder materials. Binder materials that may be used in the present disclosure can include, but are not limited to, thermoplastic binder fibers, such as PET/PE bicomponent binder fiber, and water-compatible adhesives such as, for example, latexes. In some embodiments, binder materials as used herein can be in powder form, for example, such as thermoplastic PE powder. Importantly, the binder can comprise one that is water insoluble on the dried substrate. In certain embodiments, latexes used in the present disclosure can be cationic or anionic to facilitate application to and adherence to cellulosic fibers that can be used herein. For instance, latexes believed suitable for use include, but are not limited to, anionic styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, as well as other suitable anionic latex polymers known in the art. Examples of such latexes are described in U.S. Pat. No. 4,785,030 to Hager, U.S. Pat. No. 6,462,159 to Hamada, U.S. Pat. No. 6,752,905 to Chuang et al. and so forth. Examples of suitable thermoplastic binder fibers include, but are not limited to, monocomponent and multi-component fibers having at least one relatively low melting thermoplastic polymer such as polyethylene. In certain embodiments, polyethylene/polypropylene sheath/core staple fibers can be used. Binder fibers may have lengths in line with those described herein above in relation to the synthetic cellulosic fibers.

Binders in liquid form, such as latex emulsions, can comprise between about 0% and about 10% of the foam (by weight). In certain embodiments the non-fibrous binder can comprise between about 0.1% and 10% of the foam (by weight) or even between about 0.2% and about 5% or even between about 0.5% and about 2% of the foam (by weight). Binder fibers, when used, may be added proportionally to the other components to achieve the desired fiber ratios and structure while maintaining the total solids content of the foam below the amounts stated above. As an example, in some embodiments, binder fibers can comprise between about 0% and about 50% of the total fiber weight, and more preferably, between about 5% to about 40% of the total fiber weight in some embodiments.

Foam Stabilizers

In some embodiments, if a fluid supply 16, 28 is configured as a foam the foam may optionally also include one or more foam stabilizers known in the art and that are compatible with the components of the foam and further do not interfere with the hydrogen bonding as between the cellulosic fibers. Foam stabilizing agents believed suitable for use in the present disclosure, without limitation, one or more zwitterionic compounds, amine oxides, alkylated polyalkylene oxides, or mixture or combinations thereof. Specific examples of foam stabilizers includes, without limitation, cocoamine oxide, isononyldimethylamine oxide, n-dodecyldimethylamine oxide, and so forth.

In some embodiments, if utilized, the foam stabilizer can comprise between about 0.01% and about 2% of the foam (by weight). In certain embodiments, the foam stabilizer can comprise between about 0.05% and 1% of the foam or even between about 0.1 and about 0.5% of the foam (by weight).

Components

In the methods as described herein, the foam forming process can include adding one or more components as additional additives that will be incorporated into the substrate 12. For example, one additional additive that can be added during the formation of the substrates 12 as described herein can be a superabsorbent materials (SAM). SAM is commonly provided in a particulate form and, in certain aspects, can comprise polymers of unsaturated carboxylic acids or derivatives thereof. These polymers are often rendered water insoluble, but water swellable, by crosslinking the polymer with a di- or polyfunctional internal crosslinking agent. These internally cross-linked polymers are at least partially neutralized and commonly contain pendant anionic carboxyl groups on the polymer backbone that enable the polymer to absorb aqueous fluids, such as body fluids. Typically, the SAM particles are subjected to a post-treatment to crosslink the pendant anionic carboxyl groups on the surface of the particle. SAMs are manufactured by known polymerization techniques, desirably by polymerization in aqueous solution by gel polymerization. The products of this polymerization process are aqueous polymer gels, i.e., SAM hydrogels that are reduced in size to small particles by mechanical forces, then dried using drying procedures and apparatus known in the art. The drying process is followed by pulverization of the resulting SAM particles to the desired particle size. Examples of superabsorbent materials include, but are not limited to, those described in U.S. Pat. No. 7,396,584 Azad et al., U.S. Pat. No. 7,935,860 Dodge et al., US2005/5245393 to Azad et al., US2014/09606 to Bergam et al., WO2008/027488 to Chang et al. and so forth. In addition, in order to aid processing, the SAM may be treated in order to render the material temporarily non-absorbing during the formation of the foam and formation of the highly-expanded foam. For example, in one aspect, the SAM may be treated with a water-soluble protective coating having a rate of dissolution selected such that the SAM is not substantially exposed to the aqueous carrier until the highly-expanded foam has been formed and drying operations initiated. Alternatively, in order to prevent or limit premature expansion during processing, the SAM may be introduced into the process at low temperatures.

In some embodiments incorporating SAM, the SAM can comprise between about 0% and about 40% of the foam (by weight). In certain embodiments, SAM can comprise between about 1% and about 30% of the foam (by weight) or even between about 10% and about 30% of the foam (by weight).

Other additional agents can include one or more wet strength additives that can be added to the foam or fluid supply 16, 28 in order to help improve the relative strength of the ultra-low density composite cellulosic material. Such strength additives suitable for use with paper making fibers and the manufacture of paper tissue are known in the art. Temporary wet strength additives may be cationic, nonionic or anionic. Examples of such temporary wet strength additives include PAREZ™ 631 NC and PAREZ® 725 temporary wet strength resins that are cationic glyoxylated polyacrylamides available from Cytec Industries, located at West Paterson, N.J. These and similar resins are described in U.S. Pat. No. 3,556,932 to Coscia et al. and U.S. Pat. No. 3,556,933 to Williams et al. Additional examples of temporary wet strength additives include dialdehyde starches and other aldehyde containing polymers such as those described in U.S. Pat. No. 6,224,714 to Schroeder et al.; U.S. Pat. No. 6,274,667 to Shannon et al.; U.S. Pat. No. 6,287,418 to Schroeder et al.; and U.S. Pat. No. 6,365,667 to Shannon et al., and so forth.

Permanent wet strength agents comprising cationic oligomeric or polymeric resins may also be used in the present disclosure. Polyamide-polyamine-epichlorohydrin type resins such as KYMENE 557H sold by Solenis are the most widely used permanent wet-strength agents and are suitable for use in the present disclosure. Such materials have been described in the following U.S. Pat. No. 3,700,623 to Keim; U.S. Pat. No. 3,772,076 to Keim; U.S. Pat. No. 3,855,158 to Petrovich et al.; U.S. Pat. No. 3,899,388 to Petrovich et al.; U.S. Pat. No. 4,129,528 to Petrovich et al.; U.S. Pat. No. 4,147,586 to Petrovich et al.; U.S. Pat. No. 4,222,921 to van Eenam and so forth. Other cationic resins include polyethylenimine resins and aminoplast resins obtained by reaction of formaldehyde with melamine or urea. Permanent and temporary wet strength resins may be used together in the manufacture of composite cellulosic products of the present disclosure. Further, dry strength resins may also optionally be applied to the composite cellulosic webs of the present disclosure. Such materials may include, but are not limited to, modified starches and other polysaccharides such as cationic, amphoteric, and anionic starches and guar and locust bean gums, modified polyacrylamides, carboxymethylcellulose, sugars, polyvinyl alcohol, chitosan, and the like.

If used, such wet and dry strength additives can comprise between about 0.01 and about 5% of the dry weight of cellulose fibers. In certain embodiments, the strength additives can comprise between about 0.05% and about 2% of the dry weight of cellulose fibers or even between about 0.1% and about 1% of the dry weight of cellulose fibers.

Still other additional components may be added to the foam so long as they do not significantly interfere with the formation of the highly-expanded stable foam, the hydrogen bonding as between the cellulosic fibers or other desired properties of the web. As examples, additional additives may include one or more pigments, opacifying agents, antimicrobial agents, pH modifiers, skin benefit agents, odor absorbing agents, fragrances, thermally expandable microspheres, foam particles (such as, pulverized foam particles), and so forth as desired to impart or improve one or more physical or aesthetic attributes. In certain embodiments the composite cellulosic webs may include skin benefit agents such as, for example, antioxidants, astringents, conditioners, emollients, deodorants, external analgesics, film formers, humectants, hydrotropes, pH modifiers, surface modifiers, skin protectants, and so forth.

When employed, miscellaneous components desirably comprise less than about 2% of the foam (by weight) and still more desirably less than about 1% of the foam (by weight) and even less than about 0.5% of the foam (by weight).

In some embodiments, the solids content, including the fibers or particulates contained herein, desirably comprise no more than about 40% of the foam. In certain embodiments the cellulosic fibers can comprise between about 0.1% and about 5% of the foam or between about 0.2 and about 4% of the foam or even between about 0.5% and about 2% of the foam.

The methods and apparatuses 10, 110, 210 as described herein can be beneficial for forming one or more components of personal care products. For example, in one embodiment, the substrates 12 described herein can be an absorbent core for an absorbent article, such as, but not limited to, a diaper, adult incontinence garment, or feminine care product. The substrates 12 as described herein may also be beneficial for using in other products, such as, but not limited to facial tissues, wipes, and wipers.

Embodiments

Embodiment 1: A headbox including a machine direction and a cross direction, the headbox comprising at least one flow section, the at least one flow section comprising: a bottom surface; a top surface, the top surface being opposite from the bottom surface; a first side; and a second side, the second side being opposite from the first side and spaced apart from the first side in the cross direction; wherein the first side and the second side each comprise: a first portion being convex to an interior of the at least one flow section; and a second portion being concave to the interior of the at least one flow section.

Embodiment 2: The headbox of embodiment 1, wherein the at least one flow section further comprises: an inlet; and an outlet; wherein the first portion is closer to the inlet than is the second portion.

Embodiment 3: The headbox of embodiment 2, wherein a width of the at least one flow section at the inlet is less than a width of the at least one flow section at the outlet.

Embodiment 4: The headbox of any one of the preceding embodiments, wherein the first side and the second side each further comprise a flow spreading portion, the flow spreading portion being closer to the inlet than is the first portion and providing an increasing width in the flow section away from the inlet.

Embodiment 5: The headbox of any one of the preceding embodiment s, wherein the first portion and the second portion each include a changing radius of curvature along a machine direction length of the first portion and the second portion.

Embodiment 6: The headbox of embodiment 2 or 3, wherein the interior includes a height, the height at the inlet being greater than the height at the outlet.

Embodiment 7: The headbox of any one of the preceding embodiments, wherein the first side and the second side are symmetric about an axis parallel to the machine direction.

Embodiment 8: The headbox of any one of the preceding embodiments, wherein the first side and the second side each comprise an inflection segment.

Embodiment 9: The headbox of embodiment 8, wherein the inflection segment provides a transition between the first portion and the second portion.

Embodiment 10: The headbox of any one of the preceding embodiments, wherein the at least one flow section comprises a first flow section and a second flow section.

Embodiment 11: The headbox of embodiment 10, wherein the first flow section and the second flow section are spaced apart from one another in the cross direction.

Embodiment 12: A headbox including a machine direction and a cross direction, the headbox comprising a first flow section and a second flow section, the first flow section and second flow section each comprising: a bottom surface; a top surface, the top surface being opposite from the bottom surface; a first side; and a second side, the second side being opposite from the first side and spaced apart from the first side in the cross direction; wherein the first side and the second side each comprise: a first portion being convex to an interior of the at least one flow section; and a second portion being concave to the interior of the at least one flow section.

Embodiment 13: The headbox of embodiment 12, the first flow section and the second flow section each further comprise: an inlet; and an outlet; wherein the first portion is closer to the inlet than is the second portion.

Embodiment 14: The headbox of embodiment 13, wherein the first flow section and second flow section are each configured such that a width of the interior at the inlet is less than a width of the interior at the outlet.

Embodiment 15: The headbox of any one of embodiments 12-14, wherein the first side and the second side are symmetric about an axis parallel to the machine direction.

Embodiment 16: The headbox of any one of embodiments 12-15, wherein the first side and the second side each comprise an inflection segment providing a transition between the first portion and the second portion.

Embodiment 17: A headbox including a machine direction and a cross direction, the headbox comprising at least one flow section, the at least one flow section comprising an interior, the interior comprising a machine directional side profile including a first side profile and a second side profile, the second side profile being opposite from the first side profile and spaced apart from the first side profile in the cross direction, the first side profile and the second side profile each comprising: a first portion being convex to the interior of the at least one flow section; and a second portion being concave to the interior of the at least one flow section.

Embodiment 18: The headbox of embodiment 17, further comprising: an inlet; and an outlet; wherein the first portion is closer to the inlet than is the second portion.

Embodiment 19: The headbox of embodiment 17 or 18, wherein the at least one flow section further comprises: a bottom surface; a top surface, the top surface being opposite from the bottom surface; a first side; and a second side, the second side being opposite from the first side and spaced apart from the first side in the cross direction; wherein the first side provides the first side profile and wherein the second side provides the second side profile.

Embodiment 20: The headbox of any one of embodiments 17-19, wherein the first side profile and the second side profile each comprise an inflection segment providing a transition between the first portion and the second portion.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A headbox including a machine direction and a cross direction, the headbox comprising at least one flow section, the at least one flow section comprising:
    an inlet;
    an outlet;
    a bottom surface;
    a top surface, the top surface being opposite from the bottom surface;
    a first side; and
    a second side, the second side being opposite from the first side and spaced apart from the first side in the cross direction;
    wherein the first side and the second side each comprise:
        a first portion being convex to an interior of the at least one flow section;
        a second portion being concave to the interior of the at least one flow section, wherein the first portion is closer to the inlet than is the second portion; and
    wherein a width of the at least one flow section at the inlet is less than a width of the at least one flow section at the outlet; and
    wherein the interior further includes a height, the height at the inlet being greater than the height at the outlet.

2. The headbox of claim 1, wherein the first side and the second side each further comprise a flow spreading portion, the flow spreading portion being closer to the inlet than is the first portion and providing an increasing width in the flow section away from the inlet.

3. The headbox of claim 1, wherein the first portion and the second portion each include a changing radius of curvature along a machine direction length of the first portion and the second portion.

4. The headbox of claim 1, wherein the first side and the second side each comprise an inflection segment.

5. The headbox of claim 4, wherein the inflection segment provides a transition between the first portion and the second portion.

6. The headbox of claim 1, wherein the at least one flow section comprises a first flow section and a second flow section.

7. The headbox of claim 6, wherein the first flow section and the second flow section are spaced apart from one another in the cross direction.

8. A headbox including a machine direction and a cross direction, the headbox comprising at least one flow section, the at least one flow section comprising:
    an inlet;
    an outlet;
    a bottom surface;
    a top surface;
    a first side;
    a second side, the second side being opposite from the first side and spaced apart from the first side in the cross direction; and an interior, wherein a flow path of the interior at the inlet provides an increasing width in the cross direction in the flow section away from the inlet;

wherein the first side and the second side each comprise:
a first portion being convex to the interior; and
a second portion being concave to the interior; wherein the first portion is closer to the inlet than is the second portion.

9. The headbox of claim 8, wherein a width of the interior at the inlet is less than a width of the interior at the outlet.

10. The headbox of claim 8, wherein the interior includes a height, the height at the inlet being greater than the height at the outlet.

11. The headbox of claim 8, wherein the first side and the second side each comprise an inflection segment providing a transition between the first portion and the second portion.

12. A headbox including a machine direction and a cross direction, the headbox comprising at least one flow section, the at least one flow section comprising:
an inlet;
an outlet;
a bottom surface;
a top surface; and
an interior, the interior comprising a machine directional side profile including a first side profile and a second side profile, the second side profile being opposite from the first side profile and spaced apart from the first side profile in the cross direction, the first side profile and the second side profile each comprising:
a first portion being convex to the interior of the at least one flow section; and
a second portion being concave to the interior of the at least one flow section, wherein the first portion is closer to the inlet than is the second portion; and
wherein the top surface and the bottom surface are configured to provide an arcing shape in a z-direction between the top surface and the bottom surface.

13. The headbox of claim 12, wherein the at least one flow section further comprises:
a first side; and
a second side, the second side being opposite from the first side and spaced apart from the first side in the cross direction;
wherein the first side provides the first side profile and wherein the second side provides the second side profile.

14. The headbox of claim 12, wherein the top surface comprises a curved shape and the bottom surface includes a curved shape.

15. The headbox of claim 12, wherein a width of the interior at the inlet is less than a width of the interior at the outlet.

16. The headbox of claim 12, wherein the interior includes a height, the height at the inlet being greater than the height at the outlet.

17. The headbox of claim 12, wherein a flow path of the interior at the inlet provides an increasing width in the cross direction away from the inlet.

18. The headbox of claim 12, wherein the first side profile and the second side profile each further comprise a flow spreading portion, the flow spreading portion being closer to the inlet than is the first portion and providing an increasing width in the flow section away from the inlet.

19. A headbox including a machine direction and a cross direction, the headbox comprising at least one flow section, the at least one flow section comprising:
an inlet;
an outlet;
a bottom surface;
a top surface; and
an interior, the interior comprising a machine directional side profile including a first side profile and a second side profile, the second side profile being opposite from the first side profile and spaced apart from the first side profile in the cross direction, wherein a width of the at least one flow section at the inlet is less than a width of the at least one flow section at the outlet;
wherein the interior further includes a height, the height at the inlet being greater than the height at the outlet; and
wherein the top surface and the bottom surface are configured to provide an arcing shape in a z-direction between the top surface and the bottom surface.

20. The headbox of claim 19, wherein the first side profile and the second side profile each comprise:
a first portion being convex to the interior of the at least one flow section; and
a second portion being concave to the interior of the at least one flow section, wherein the first portion is closer to the inlet than is the second portion.

* * * * *